United States Patent
Kennedy et al.

(10) Patent No.: US 6,605,753 B1
(45) Date of Patent: Aug. 12, 2003

(54) PROTEIN TYROSINE PHOSPHATE-1B (PTP-1B) DEFICIENT MICE AND USES THEREOF

(75) Inventors: Brian Kennedy, Kirkland (CA); Paul Payette, St. Laurent (CA); Michael Gresser, Les Cedres (CA); Chidambaram Ramachandran, Pierrefonds (CA); Michel Tremblay, Dorval (CA); Mounib Elchebly, Montreal (CA)

(73) Assignees: Merck & Co., Inc., Rahway, NJ (US); McGill University, Quebec (CA)

( * ) Notice: Subject to any disclaimer, the term of this patent is extended or adjusted under 35 U.S.C. 154(b) by 0 days.

(21) Appl. No.: 09/744,383
(22) PCT Filed: Jul. 23, 1999
(86) PCT No.: PCT/CA99/00675
§ 371 (c)(1),
(2), (4) Date: Jan. 23, 2001
(87) PCT Pub. No.: WO00/06712
PCT Pub. Date: Feb. 10, 2000

Related U.S. Application Data

(60) Provisional application No. 60/093,975, filed on Jul. 24, 1998.
(51) Int. Cl.[7] ............... A01K 67/027; A01K 67/00; C12N 15/00; C12N 15/09; C12N 15/63
(52) U.S. Cl. ............... 800/18; 800/8; 800/13; 800/21; 800/22; 435/455; 435/463; 435/325
(58) Field of Search ............... 435/455, 463, 435/320.1, 325; 800/3, 18, 21, 22, 25, 13, 8

(56) References Cited

PUBLICATIONS

Ryan et.al.; Use of Transgenic and Knockout Strategies in Mice, 2002, Seminars in Nephrology, vol. 22: 154–160.*

Holschneider et.al.; Genotype to phenotype: challenges and opportunities, 2000, Int. J. Devl. Neuroscience 18: 615–618.*

Evans et.al.; Establishment in culture of pluipotential cells from mouse embryos, 1981, Nature, vol. 292: 154–156.*

* cited by examiner

Primary Examiner—Deborah Crouch
Assistant Examiner—Thai-An N. Ton
(74) Attorney, Agent, or Firm—Joan E. Switzer; Joanne M. Giesser

(57) ABSTRACT

The present invention provides mice that have had their PTP-1B genes disrupted by targeted homologous recombination. The mice have no detectable PTP-1B protein, yet appear to be physiologically normal. However, in the fed state on a normal diet, the mice have half the level of circulating insulin as their wild-type littermates. In glucose and insulin tolerance tests, the mice show an increased insulin sensitivity. When fed a high fat, high carbohydrate diet, the mice show a resistance to weight gain as compared to their wild-type littermates. Methods making the mice and cell lines derived from the mice are also provided. The present invention also provides methods of identifying inhibitors of the enzymatic activity of PTP-1B as well as inhibitors identified by such methods.

13 Claims, 11 Drawing Sheets

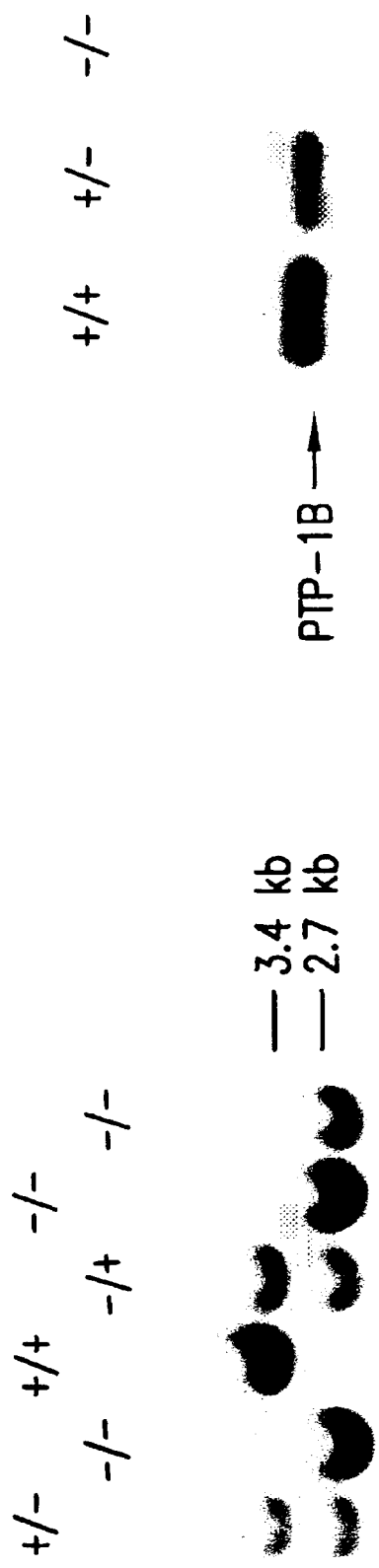

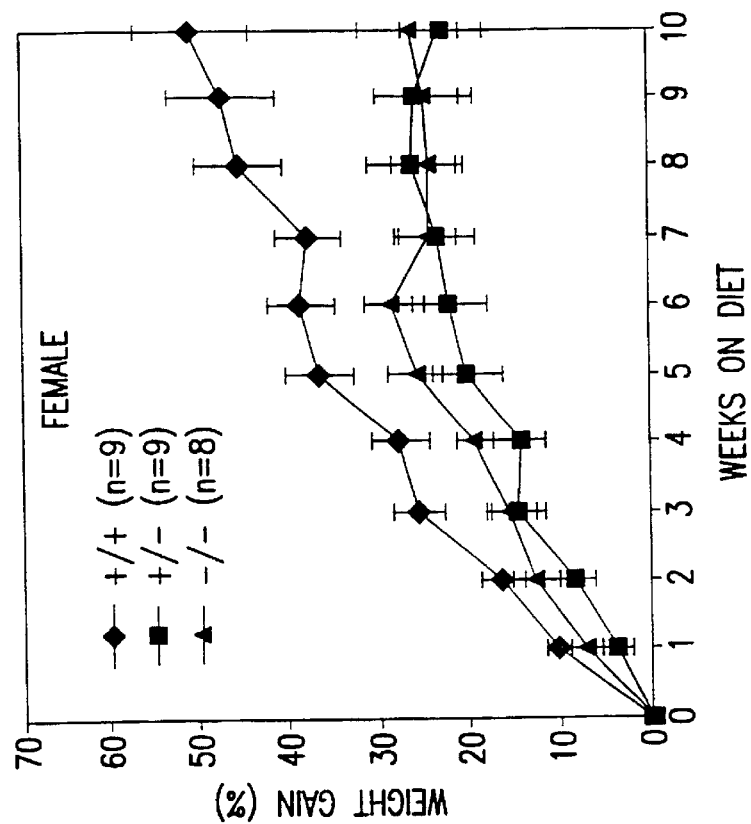
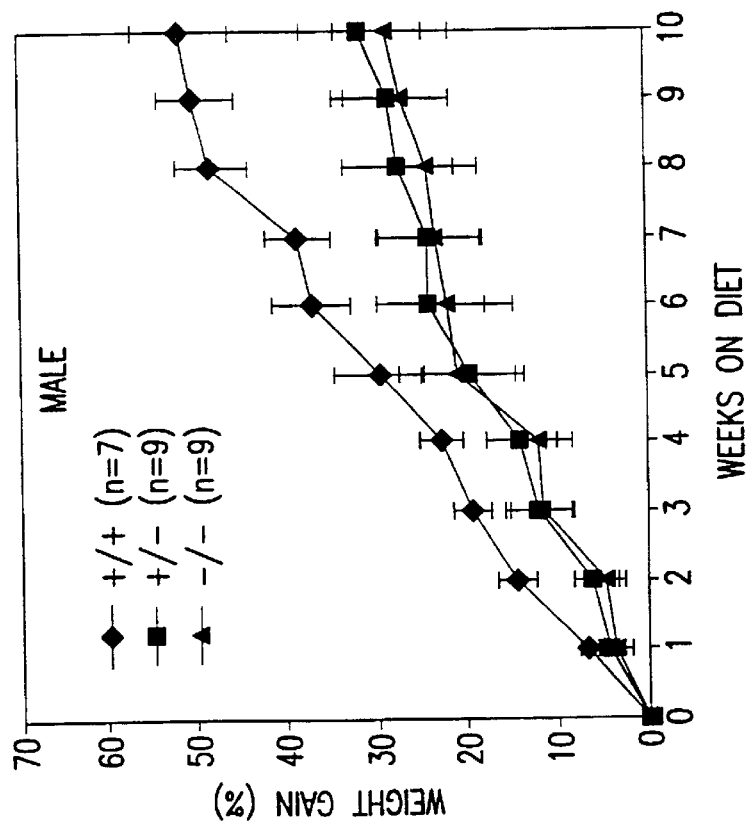
FIG. 5B
FIG. 5A

+/+ IWAT    −/− IWAT

+/+ IBAT    −/− IBAT

PROTEIN TYROSINE PHOSPHATE-1B (PTP-1B) DEFICIENT MICE AND USES THEREOF

CROSS-REFERENCE TO RELATED APPLICATIONS

This is a U.S. national filing under 35 U.S.C. §371 of PCT/CA99/00675, filed Jul. 23, 1999 and which published as WO 00/06712 on Feb. 10, 2000, and which claims the benefit of U.S. Provisional Patent Application No. 60/093,975, filed on Jul. 24, 1998.

STATEMENT REGARDING FEDERALLY-SPONSORED R&D

Not applicable

REFERENCE TO MICROFICHE APPENDIX

Not applicable

FIELD OF THE INVENTION

The invention is directed to the field of transgenic mice containing a disrupted PTP-1B gene. The mice may contain a disruption in either one or both copies of the PTP-1B gene. In the case of mice containing a disruption in both copies of the PTP-1B gene, such mice lack detectable expression of PTP-1B protein.

BACKGROUND OF THE INVENTION

Protein tyrosine phosphatases (PTPases) are a large family of transmembrane or intracellular enzymes that dephosphorylate substrates involved in a variety of regulatory processes (Fischer et al., 1991, Science 253:401–406). Protein tyrosine phosphatase-1B (PTP-1B) is a ~50 kd intracellular protein present in abundant amounts in various human tissues (Charbonneau et al., 1989, Proc. Natl. Acad. Sci. USA 86:5252–5256; Goldstein, 1993, Receptor 3:1–15). Like other PTPases, PTP-1B has a catalytic domain characterized by the sequence motif (I/V)HCXAGXXR(S/T)G (SEQ.ID.NO.:1), containing arginine and cysteine residues that are critical to the enzyme's activity (Streuli et al., 1990, EMBO J. 9:2399–2407; Guan et al., 1990, Proc. Natl. Acad. Sci. USA 87:1501–1505; Guan & Dixon, 1991, J. Biol. Chem. 266:17026–17030). The amino terminal 35 amino acid residues of PTP-1B localize the protein to the endoplasmic reticulum (Frangioni et al., 1992, Cell 68:545–560).

Determining which proteins are substrates of PTP-1B has been of considerable interest. One substrate which has aroused special interest is the insulin receptor. The binding of insulin to the insulin receptor results in autophosphorylation of the receptor, most notably on tyrosines 1146, 1150, and 1151 in the kinase catalytic domain (White & Kahn, 1994, J. Biol. Chem. 269:1–4). This causes activation of the insulin receptor tyrosine kinase, which phosphorylates the various insulin receptor substrate (IRS) proteins that propagate the insulin signaling event further downstream to mediate insulin's various biological effects.

Seely et al., 1996, Diabetes 45:1379–1385 (Seely) studied the relationship of PTP-1B and the insulin receptor in vitro. Seely constructed a glutathione S-transferase (GST) fusion protein of PTP-1B that had a point mutation in the PTP-1B catalytic domain. Although catalytically inactive, this fusion protein was able to bind to the insulin receptor, as demonstrated by its ability to precipitate the insulin receptor from purified receptor preparations and from whole cell lysates derived from cells expressing the insulin receptor.

Ahmad et al., 1995, J. Biol. Chem. 270:20503–20508 used osmotic loading to introduce PTP-1B neutralizing antibodies into rat KRC-7 hepatoma cells. The presence of the antibody in the cells resulted in an increase of 42% and 38%, respectively, in insulin stimulated DNA synthesis and phosphatidyinositol 3' kinase activity. Insulin receptor autophosphorylation and insulin receptor substrate-1 tyrosine phosphorylation were increased 2.2 and 2.0-fold, respectively, in the antibody-loaded cells. The antibody-loaded cells also showed a 57% increase in insulin stimulated insulin receptor kinase activity toward exogenous peptide substrates.

Until the present invention, studies of the interaction of PTP-1B and the insulin receptor were limited to studies conducted on cell-free preparations of PTP-1B or in cultured cell lines. Therefore, such studies did not address the issue of whether PTP-1B activity affects the regulation of the insulin receptor in a way that results in physiological effects on glucose metabolism, triglyceride metabolism, or weight gain in living mammals. Because of the complexity of the regulation of the insulin receptor and its interactions with proteins such as PTP-1B, there is a need to study this regulation in an environment that is as close as possible to that of a living mammal. The knockout mice of the present invention are useful in helping to meet this need. The knockout mice of the present invention also are useful in that they provide an animal model that can be used in the design and assessment, in a living mammal, of compounds that modulate insulin receptor activity.

SUMMARY OF THE INVENTION

The present invention provides mice that have had their PTP-1B genes disrupted by targeted homologous recombination. When both copies of their PTP-1B genes are disrupted, the mice have no detectable PTP-1B protein, yet appear to be physiologically normal. However, in the fed state, the mice have slightly lower glucose levels and half the level of circulating insulin as their wild-type littermates. In glucose and insulin tolerance tests, the mice show increased insulin sensitivity. When fed a high fat, high carbohydrate diet, the mice, although much more insulin-sensitive than wild-type controls, are obesity-resistant.

Methods of making the mice and cell lines derived from the mice are also provided.

The present invention also provides methods of identifying inhibitors of the enzymatic activity of PTP-1B as well as inhibitors identified by such methods.

BRIEF DESCRIPTION OF THE DRAWINGS

FIG. 5. Weight gain in A) male and B) female null knockout, heterozygous knockout, and wild-type mice fed a high fat, high carbohydrate diet. A) male mice; ♦=wild-type, n=7; ■=heterozygotes, n=9; ▲=nulls, n=8. B) female mice; ♦=wild-type, n=9; ■=heterozygotes, n=9; ▲=nulls, n=8.

DETAILED DESCRIPTION OF THE INVENTION

Figure 1A:
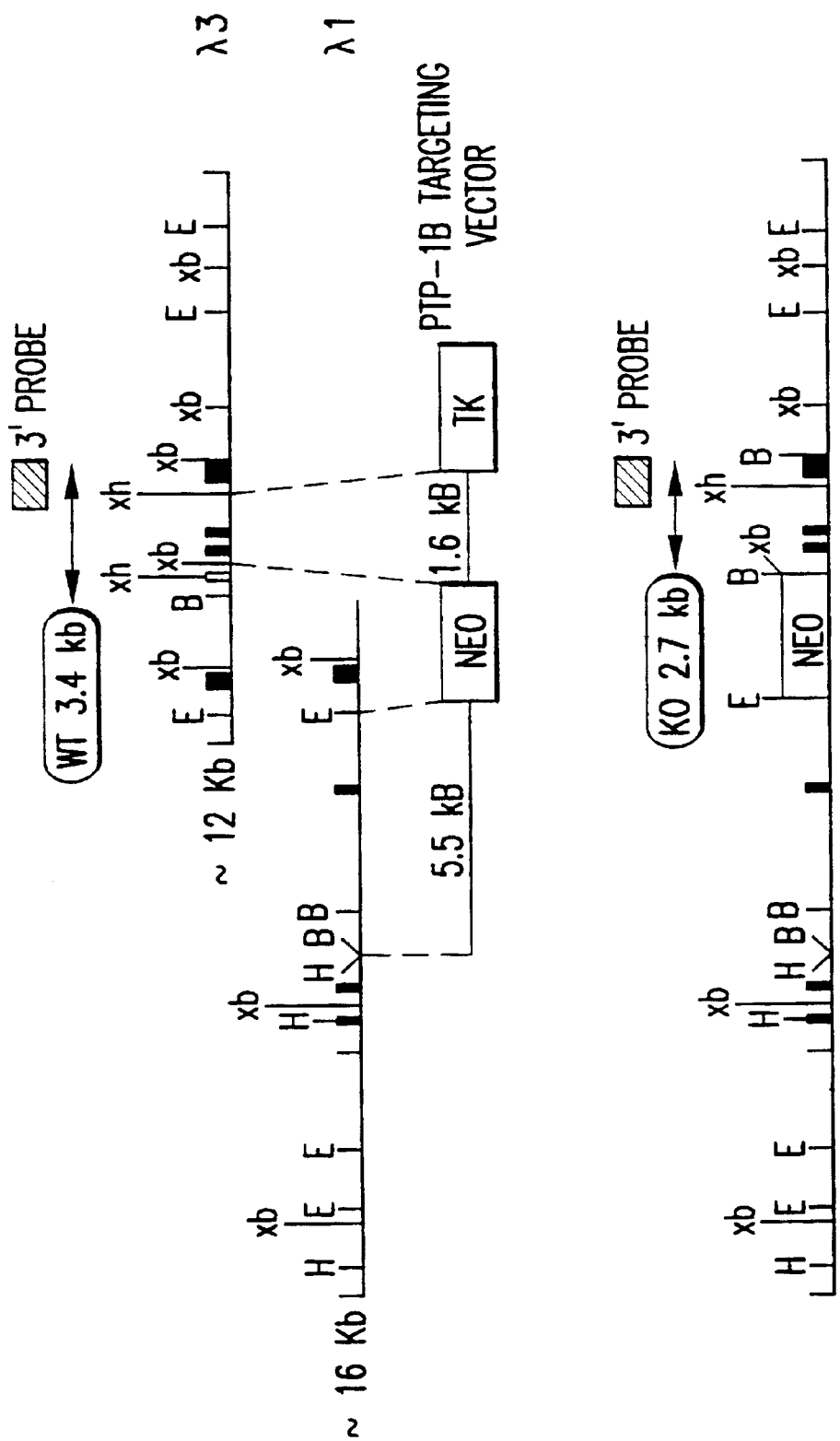
FIG. 1. Gene targeting of the PTP-1B locus. A) Genomic organization of the mouse PTP-1B gene and design of targeting vector. Exons are indicated by boxes and exon 6, which contains the active site cysteine, is unfilled. Restriction endonuclease recognition sites are abbreviated as follows: B=BamHI; E=EcoRI; H=HindIII; Xb=XbaI; Xh=XhoI. Bottom is the genomic structure of a homologous recombination event. B) Representative genomic Southern blot using the PTP-1B 3' probe on tail DNA digested with BamHI from a heterozygous cross resulting in wild type (+/+), heterozygous (+/−), and homozygous ("null") (−/−) PTP-1B offspring. C) PTP-1B immunoblot analysis of liver membrane samples from PTP-1B (+/+), PTP-1B (+/−), and PTP-1B (−/−) mice.

For the purposes of this invention:

A "transgenic mouse" is any mouse containing one or more cells bearing genetic information altered or received, directly or indirectly, by deliberate genetic manipulation at a subcellular level, such as by targeted homologous recombination, microinjection, or infection with recombinant virus. The term "transgenic mouse" is not intended to encompass classical cross-breeding or in vitro fertilization, but rather is meant to encompass mice in which one or more cells are altered by or receive a recombinant DNA molecule. A transgenic mouse can have the genetic alteration or genetic information introduced into a germ line cell, thereby conferring the ability to transfer the genetic information to offspring. If such offspring possess some or all of that alteration or genetic information, then they, too, are transgenic mice.

A "knockout mouse" is a mouse in which the expression of a preselected gene has been suppressed or eliminated by introducing into the genomic DNA of the mouse a new DNA sequence that serves to disrupt some portion of the DNA sequence of the preselected gene. A knockout mouse may have both copies of the preselected gene disrupted, in which case it is a homozygous or "null" knockout mouse. A knockout mouse may have only a single copy of the preselected gene disrupted, in which case it is a "heterozygous" knockout mouse.

One approach to the problem of determining the role of a particular gene in a biochemical pathway or a disease state is to selectively inactivate the native wild-type gene in totipotent ES cells and then generate transgenic mice using those ES cells. Such transgenic mice, having that particular gene inactivated, are known as "knockout mice." The use of gene-targeted ES cells in the generation of gene-targeted transgenic knockout mice is described in, e.g., Thomas et al., 1987, Cell 51:503–512, and is reviewed elsewhere (Frohman et al., 1989, Cell 56:145–147; Capecchi, 1989, Trends in Genet. 5:70–76; Baribault et al., 1989, Mol. Biol. Med. 6:481–492).

Techniques are available to inactivate or alter any genetic region to virtually any mutation desired by using targeted homologous recombination to insert specific changes into chromosomal genes. Generally, use is made of a "targeting vector," i.e., a plasmid containing part of the genetic region it is desired to mutate. By virtue of the homology between this part of the genetic region on the plasmid and the corresponding genetic region on the chromosome, homologous recombination can be used to insert the plasmid into the genetic region, thus disrupting the genetic region. Usually, the targeting vector contains a selectable marker gene as well.

In comparison with homologous extrachromosomal recombination, which occurs at frequencies approaching 100%, homologous plasmid-chromosome recombination was originally reported to only be detected at frequencies between $10^{-6}$ and $10^{-3}$ (Lin et al., 1985, Proc. Natl. Acad. Sci. USA 82:1391–1395; Smithies et al., 1985, Nature 317:230–234; Thomas et al., 1986, Cell 44:419–428). Non-homologous plasmid-chromosome interactions are more frequent, occurring at levels $10^5$-fold (Lin et al., 1985, Proc. Natl. Acad. Sci. USA 82:1391–1395) to $10^2$-fold (Thomas et al., 1986, Cell 44:419–428) greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening individual clones (Kim et al., 1988, Nucleic Acids Res. 16:8887–8903; Kim et al., 1991, Gene 103:227–233). Alternatively, a positive genetic selection approach has been developed in which a marker gene is constructed which will only be active if homologous insertion occurs, allowing these recombinants to be selected directly (Sedivy et al., 1989, Proc. Natl. Acad. Sci. USA 86:227–231). One of the most powerful approaches developed for selecting homologous recombinants is the positive-negative selection (PNS) method developed for genes for which no direct selection of the alteration exists (Mansour et al., 1988. Nature 336:348–352; Capecchi, 1989, Science 244:1288–1292; Capecchi, 1989, Trends in Genet. 5:70–76). The PNS method is more efficient for targeting genes which are not expressed at high levels because the marker gene has its own promoter. Nonhomologous recombinants are selected against by using the Herpes Simplex virus thymidine kinase (HSV-TK) gene and selecting against its nonhomologous insertion with herpes drugs such as gancyclovir (GANC) or FIAU (1-(2-deoxy 2-fluoro-B-D-arabinofluranosyl)-5-iodouracil). By this counter-selection, the percentage of homologous recombinants in the surviving transformants can be increased.

The present invention provides mice that have had their PTP-1B genes disrupted by targeted homologous recombination. In the case of mice that have had both copies of their PTP-1B genes disrupted ("null" mice), the mice have no detectable PTP-1B protein, yet appear to be physiologically normal. However, in the fed state, the null mice have slightly lower glucose levels and half the level of circulating insulin as their wild-type littermates. In glucose and insulin tolerance tests, the null mice show an increased insulin sensitivity. Furthermore, hyperphosphorylation of the insulin receptor is evident in the liver and muscle of the null mice injected with insulin when compared to wild-type mice treated similarly. These results indicate that PTP-1B is involved in the insulin signaling pathway in living mammals and has a role in the dephosphorylation and hence inactivation of the insulin receptor.

The PTP-1B knockout mice of the present invention are useful as sources of cell lines that do not contain functional PTP-1B protein. Such cell lines can be transfected with the human PTP-1B gene to produce cell lines expressing human PTP-1B free from interference caused by the expression of endogenous mouse PTP-1B. Such cell lines can be used in assays to identify activators or inhibitors of human PTP-1B. Accordingly, in addition to PTP-1B knockout mice, the present invention provides cell lines derived from the PTP-1B knockout mice of the present invention. Such cell lines can be produced by methods well known in the art (Williams et al., 1988, Mol. Cell. Biol. 8:3864–3871; Aaronson & Todaro, 1968, J. Cell. Physiol. 72:141–148: Jenkins et al., 1984, Nature 312:651–654).

The PTP-1B knockout mice of the present invention are useful as negative controls in assays that monitor the effects of pharmaceuticals that modulate glucose metabolism, triglyceride metabolism, or weight gain through an effect of the pharmaceuticals on PTP-1B in wild-type mice. The use of PTP-1B knockout mice as negative controls in such assays allows one to determine that an effect on glucose metabolism, triglyceride metabolism, or weight gain caused by a pharmaceutical in wild-type mice that is suspected of being caused by the action of the pharmaceutical on PTP-1B activity is actually so caused.

The PTP-1B knockout mice of the present invention are useful in assays to identify weak agonists of the insulin receptor. Since these knockout mice lack PTP-1B, they lack an important element involved in dampening the signal of the insulin receptor. Thus, in the absence of PTP-1B in the knockout mice, weak agonists of the insulin receptor can be identified where the effects of those weak agonists would have been missed in the presence of PTP-1B. Such weak agonists can be used as lead compounds which can be modified by medicinal chemistry to develop stronger, pharmacologically useful, agonists of the insulin receptor.

The PTP-1B knockout mice of the present invention are useful for studying the role of the insulin receptor in various aspects of metabolism or physiology. For example, the mice can be monitored to determine if the loss of PTP-1B has any effect on their longevity. In C. elegans, mutations in the gene daf-2 affect longevity. Daf-2 is a homolog of the mammalian insulin receptor.

Db/db mice develop many complications, such as peripheral neuropathies and myocardial disease, similar to those of humans with diabetes. The PTP-1B knockout mice of the present invention can be crossed with db/db mice in order to better study the relationship between PTP-1B activity and diabetes. The PTP-1B knockout mice of the present invention can be used in a similar manner with other chemically or genetically induced diabetic mouse models.

It will be of interest to investigate the effects of glucose levelling drugs such as thiazolidinediones or sulfonylureas in the PTP-1B knockout mice of the resent invention.

In view of the demonstration herein that PTP-1B regulation of the insulin receptor may have a role in obesity, it will be of interest to investigate the effects of leptin, the melanocortin-4 receptor, the neuropcptide $Y_5$ receptor, and other molecular species that have been implicated in weight control in PTP-1B knockout mice.

A variety of methods can be used to produce the knockout mice of the present invention. One method involves introducing a transgene into target cells that are then incorporated into blastocyts that are implanted into pseudopregnant female mice. A type of target cell for transgene introduction is the embryonal stem cell (ES). ES cells may be obtained from pre-implantation embryos cultured in vitro (Evans et al., 1981, Nature 292: 154–156; Bradley et al., 1984, Nature 309: 255–258; Gossler et al., 1986, Proc. Natl. Acad. Sci. USA 83: 9065–9069; Robertson et al., 1986, Nature 322, 445–448; Wood et al., 1993, Proc. Natl. Acad. Sci. USA 90: 4582–4584). Transgenes can be efficiently introduced into ES cells by standard techniques such as DNA transfection or by retrovirus-mediated transduction. The resultant transformed ES cells can thereafter be combined with blastocysts from a mouse. Following implantation of the blastocyts into pseudopregnant foster mothers, the introduced ES cells can thereafter colonize the embryos that develop from the blastocyts and contribute to the germ line of the resulting chimeric mice (Jaenisch, 1988, Science 240: 1468–1474).

Another method that can be used to produce the knockout mice of the present invention involves microinjecting the transgene into the male proinucleus of a ferilized egg (Brinster et al., 1981, Cell 27:223; Wagner et al., 1981, Proc. Natl. Acad. Sci. USA 78:5016; Sterwart et al., 1982, Science 217:1046–1048; Townes et al., 1985, EMBO J. 4:1715). The microinjected transgene integrates into the DNA of the male pronucleus of the fertilized egg. The ferilized egg is then implanted into a recipient female mouse and allowed to develop. If this procedure is successful, the resulting embryo will contain the transgene in all its cells. Occasionally, the fertilized egg will divide before the transgene integrates into the genome. In such cases, chimeric embryos will be produced. Such chimeric embryos will contain the transgene in some, but not all, of their cells.

The present invention provides a method of producing a mouse, at least some of whose cells contain an altered gene encoding an altered form of protein tyrosine phosphatase-1B (PTP-1B), the altered gene having been targeted to replace the wild-type PTP-1B gene in the mouse, the method comprising:

(a) providing an altered gene encoding an altered form of PTP-1B designed to target the PTP-1B gene of mouse embryonic stem (ES) cells;

(b) introducing the altered gene encoding an altered form of PTP-1B into mouse ES cells;

(c) selecting ES cells in which the altered gene encoding an altered form of PTP-1B has disrupted the wild-type PTP-1B gene;

(d) injecting the ES cells from step (c) into mouse blastocyts;

(e) implanting the blastocysts from step (d) into a pseudopregnant mouse;

(f) allowing the blastocytsts to develop into embryos and allowing the embryos to develop to term in order to produce a mouse at least some of whose cells contain an altered gene encoding an altered form of PTP-1B.

In the case where the mice produced by the above-described method contain germ cells with the altered gene encoding an altered form of PTP-1B, the mice may be mated to produce mice all of whose somatic cells as well as germ cells contain the altered gene encoding an altered form of PTP-1B. Mice having germ cells containing the altered gene encoding an altered form of PTP-1B can be mated to produce homozygous, or "null," mice that contain disruptions in both copies of their PTP-1B genes and thus have no detectable PTP-1B activity.

The knockout mice of the present invention have altered glucose and fat metabolism compared to wild-type mice. The effect of the disruption of the PTP-1B gene in the knockout mice of the present invention demonstrates that altering the activity of PTP-1B can modulate insulin signaling in vivo, i.e., in a living mammal. The knockout mice of the present invention also demonstrate that altering the activity of PTP-1B can have an effect on weight gain. These results suggest that inhibition of PTP-1B may be beneficial in the treatment of Type II diabetes (non-insulin dependent diabetes, NIDDM) and obesity. The present inventors are the first to demonstrate an effect of PTP-1B on such aspects of fuel metabolism in a living mammal as levels of blood glucose and triglycerides, or weight gain. Prior to the present invention, it was not predictable that the interaction of PTP-1B and the insulin receptor that was seen in purified enzyme preparations or in tissue culture cells could be extrapolated to effects such as these, which can only be studied in living mammals. Accordingly, before the present invention, it was not reasonably predictable that one could use inhibitors of the interaction betweeen PTP-1B and the insulin receptor to modulate levels of blood glucose or triglycerides in a living mammal, or control obesity, since the relevance of experiments done in tissue culture to the regulation of fuel metabolism in living mammals was not clear.

Prior to the work presented herein, it was not thought that such a simple change as knocking out PTP-1B alone would have such dramatic effects as those observed by the present inventors. This is because it was known that insulin receptor action is regulated in a complex manner. Among the various classes of proteins involved in this regulation, several protein tyrosine phosphatases (PTPases) alone were known to be involved. For example, Kulas et al., 1995, J. Biol. Chem. 270:2435–2438 demonstrated that insulin receptor activity is negatively regulated by the PTPase LAR. Others had shown that the PTPase SH2-PTP (aka Syp) positively regulates insulin activity (Xiao et al., 1994, J. Biol. Chem. 269:21244–21248; Milarski et al., 1994, J. Biol. Chem. 269:21239–21243; Yamauchi et al., 1995, Proc. Natl. Acad. Sci. USA 92:664–668; Noguchi et al., 1994, Mol. Cell. Biol. 14:6674–6682). Hashimoto et al., 1992. J. Biol. Chem. 267:13811–123814 demonstrated that a number of protein tyrosine phosphatases can dephosphorylate the insulin receptor in vitro as efficiently as PTP-1B. Numerous other reports demonstrate that PTPs other than PTP-1B can also dephosphorylate the activated insulin receptor (Jacob et al., 1998, J. Biol. Chem. 273:4800–4809: Chiarugi et al., 1997, Biochem. Biophys. Res. Commun. 238:676–682; Moller et al., 1995, J. Biol. Chem. 270:23126–23131).

Given such a complex regulatory mechanism as that which governs the activity of the insulin receptor, one would have expected that knocking out a single component of that mechanism in a living mammal would have produced little effect, since that single component either would have been quantitatively insignificant in itself, or since it would have been expected that other components of the regulatory mechanism would have compensated for the lack of the knocked-out component, restoring the balance of the insulin receptor activity to its normal state. See, e.g., Ahmad et al., 1995, J. Biol. Chem. 270:20503–20508, at page 20508, who sum up the results of their studies as follows: "[I]nsulin signalling is balanced at multiple levels by a number of PTPases . . . " Despite these expectations, the present invention demonstrates that it is possible to control insulin receptor activity in a living mammal through modification of the activity of PTP-1B. Accordingly, based upon the results demonstrated by the knockout mice of the present invention, it is now feasible to identify inhibitors of the enzymatic activity of PTP-1B that will be useful in modulating the activity of the insulin receptor in living mammals. Such inhibitors should have utility in the treatment of Type II diabetes and obesity.

Prior to the present invention, it was believed that while such inhibitors of PTP-1B might possibly have desirable effects on the insulin receptor, they would not be pharmacologically useful since it was believed that PTP-1B had many essential roles in addition to its role in modulating insulin receptor activity. Therefore, it was believed that in addition to possible desirable effects on the insulin receptor, inhibitors of the enzymatic activity of PTP-1B would have too many deleterious side effects to be pharmacologically useful. The prior art thus taught that inhibitors of the binding of PTP-1B to the insulin receptor might be useful (since such inhibitors would have effects specific to the insulin receptor) but inhibitors of the enzymatic activity of PTP-1B would not be useful (since such inhibitors would have more general effects). See, e.g., International Patent Publication WO 97/32595, at page 11, line 36, to page 12, line 7: "It is preferable to affect binding [of PTP-1B to the insulin receptor] rather than phosphatase activity since phosphatase activity in general is essential to the cell." Another example of how the prior art taught away from the use of inhibitors of the enzymatic activity of PTP-1B can be seen in claim 1 of U.S. Pat. No. 5,726,027, which reads: "A method for determining whether a composition inhibits protein tyrosine phosphatase 1B (PTP1B) binding to phosphorylated insulin receptor rather than phosphatase activity, said method comprising . . . "

In view of the demonstration by the present invention that PTP-1B knockout mice are physiologically normal, with the exception of altered glucose and triglyceride metabolism, as well as altered weight gain patterns when fed a high fat, high carbohydrate diet, it is clear that the prior art was mistaken when it assumed that inhibitors of PTP-1B enzymatic activity would lack utility. The present invention makes it clear that inhibitors of PTP-1B enzymatic activity are likely to have utility for the treatment of Type II diabetes and in the control of obesity. Accordingly, the present invention provides methods of identifying inhibitors of the enzymatic activity of PTP-1B as well as inhibitors so indentified by such methods.

The present invention provides a method of identifying inhibitors of the enzymatic activity of PTP-1B comprising:
(a) providing an enzymatically active preparation of PTP-1B;
(b) measuring the enzymatic activity of PTP-1B in the enzymatically active preparation of PTP-1B in the presence and in the absence of a substance suspected of being an inhibitor of the enzymatic activity of PTP-1B;
where a decrease in the enzymatic activity of PTP-1B in the presence as compared to the absence of the substance indicates that the substance is an inhibitor of the enzymatic activity of PTP-1B.

Of course, the above-described method may be practiced in such a manner that step (b) is carried out with not just a single substance suspected of being an inhibitor of the enzymatic activity of PTP-1B, but rather with a plurality of substances suspected of being inhibitors of the enzymatic activity of PTP-1B. An example of the practice of the method in this manner would be the screening of a library of compounds, e.g., a combinatorial library, against the enzymatically active preparation of PTP-1B. In such cases, typically only a small fraction of the substances in the library will be found to be inhibitors of the enzymatic activity of PTP-1B. If the library is large, it may be divided into conveniently small portions of substances for use in step (b).

The present invention provides a method of identifying inhibitors of the enzymatic activity of the PTP-1B protein comprising:
(a) transfecting a cell with DNA encoding the human PTP-1B protein;
(b) culturing the cells of step (a) under conditions such that PTP-1B protein is produced;
(c) measuring the enzymatic activity of the PTP-1B protein in the transfected cells in the presence and in the absence of a substance suspected of being an inhibitor of the enzymatic activity of the PTP-1B protein;
where a decrease in the enzymatic activity of the PTP-1B protein in the presence as compared to the absence of the substance indicates that the substance is an inhibitor of the enzymatic activity of the PTP-1B protein.

The above-described method may be practiced in such a manner that step (c) is carried out with not just a single substance suspected of being an inhibitor of the enzymatic activity of the PTP-1B protein, but rather with a plurality of substances suspected of being inhibitors of the enzymatic activity of the PTP-1B protein. An example of the practice of the method in this manner would be the screening of a library of compounds, e.g., a combinatorial library. In such cases, typically only a small fraction of the substances in the library will be found to be inhibitors of the enzymatic activity of the PTP-1B protein. If the library is large, it may be divided into conveniently small portions of substances for use in step (c).

The cells of step (a) may be prokaryotic or eukaryotic, mammalian or amphibian, bacterial, or yeast. Cell lines derived from mammalian species which are suitable and which are commercially available, include but are not limited to, L cells L-M(TK-) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650). COS-7 (ATCC CRL 1651), CHO-K1 (ATCC CCL61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171). In a preferred embodiment, the cells are cells that have been derived from a PTP-1B null knockout mouse of the present invention.

Transfection is meant to include any method known in the art for introducing DNA sequences encoding the PTP-1B protein into the cells. For example, transfection includes calcium phosphate or calcium chloride mediated transfection, lipofection, infection with a retroviral construct containing DNA sequences encoding the PTP-1B protein, and electroporation.

Methods of measuring the enzymatic activity of the PTP-1B protein may be carried out by any methods known in the art. For example, the dephosphorylation of the insulin receptor by PTP-1B may be measured, as in Maegawa et al., 1995, J. Biol. Chem. 270:7724–7730. See also Huyer et al., 1997, J. Biol. Chem. 272:843–851. Other methods include: measuring the activity of PTP-1B in intact cells by, e.g., immunoprecipitating the enzyme and measuring its activity with a variety of artificial substrates such as FDP, MUP, p-nitrophenylphosphate, phosphotyrosyl peptides, or $^{32}P/^{33}P$-labeled phosphopeptides or phosphoproteins. In addition, the activity of PTP-1B can be measured by following the phosphotyrosyl status not only of the insulin receptor but also of any other substrates of PTP-1B. Also, where the insulin receptor remains phosphorylated for long times, as in the liver, or where the insulin receptor is hyperphosphorylated, as in muscle, the phosphorylation state of proteins involved in the insulin cascade and the biochemical effects of that cascade will be increased. Thus, one can indirectly follow the activity of PTP-1B in intact cells by measuring such factors as: glucose transport, glycogen synthesis, amino acid transport, protein synthesis, phosphorylation status of insulin receptor substrates, P13 kinase activity, Akt kinase activity, etc.

In step (c) of the above-described method, the transfected cells may be used intact or they may be first lysed and certain fractions of the cells, or partially or wholly purified preparations of the PTP-1B protein from the cells, may be used.

The substances identified by the above-described methods are especially useful when those substances are specific inhibitors of the enzymatic activity of PTP-1B, i.e., when those substances do not also inhibit the activity of another protein tyrosine phosphatase. Accordingly, it will generally be worthwhile to take the inhibitors identified by the above-described methods and further screen them against such other protein tyrosine phosphatases as, e.g., LAR, syp, CD45, etc.

The above-described methods of identifying inhibitors of the enzymatic activity of PTP-1B can be modified so as to become methods for determining whether the substances identified by the above-described methods can be used to treat Type II diabetes and associated complications or to control obesity. This would entail taking the substances identified as inhibitors of the enzymatic activity of PTP-1B and determining whether those substances modulate glucose level or triglyceride levels in a mammal, such as a mouse, rat, or human, or whether those substances prevent or diminish obesity in a mammal, such as a mouse, rat, or human, that is fed a high fat, high carbohydrate diet.

Accordingly, the present invention provides a method of determining whether a substance modulates glucose or triglyceride levels in a mammal that comprises:
(a) providing an enzymatically active preparation of PTP-1B;
(b) measuring the enzymatic activity of PTP-1B in the enzymatically active preparation of PTP-1B in the presence and in the absence of a substance suspected of being an inhibitor of the enzymatic activity of PTP-1B, thus identifying a substance that is an inhibitor of the enzymatic activity of PTP-1B;
where a decrease in the enzymatic activity of PTP-1B in the presence as compared to the absence of the substance indicates that the substance is an inhibitor of the enzymatic activity of PTP-1B;

(c) administering the substance that is an inhibitor of the enzymatic activity of PTP-1B to a mammal;

(d) measuring the blood glucose level or triglyceride levels of the mammal in step (c) and comparing the blood glucose level or triglyceride levels of the mammal in step (c) with the blood glucose level or triglyceride levels of a mammal that has not been administered the substance that is an inhibitor of the enzymatic activity of PTP-1B;

where a difference in the blood glucose level or triglyceride levels of the mammal in step (c) as compared with the blood glucose level or triglyceride levels of the mammal that has not been administered the substance that is an inhibitor of the enzymatic activity of PTP-1B indicates that the substance modulates glucose or triglyceride levels in a mammal.

In a particular embodiment, the mammal is a mouse or rat. In another embodiment, the mammal is a human.

The present invention provides substances identified by the above-described method. Such substances are expected to have utility in the treatment of Type II diabetes and associated complications in humans.

The present invention provides a method of determining whether a substance regulates obesity in a mammal that comprises:

(a) providing an enzymatically active preparation of PTP-1B;

(b) measuring the enzymatic activity of PTP-1B in the enzymatically active preparation of PTP-1B in the presence and in the absence of a substance suspected of being an inhibitor of the enzymatic activity of PTP-1B, thus identifying a substance that is an inhibitor of the enzymatic activity of PTP-1B;

where a decrease in the enzymatic activity of PTP-1B in the presence as compared to the absence of the substance indicates that the substance is an inhibitor of the enzymatic activity of PTP-1B;

(c) administering the substance that is an inhibitor of the enzymatic activity of PTP-1B to a mammal;

(d) measuring the weight gain of the mammal in step (c) when the mammal of step (c) is fed a high fat, high carbohydrate diet and comparing the weight gain of the mammal in step (c) with the weight gain of a mammal fed a high fat, high carbohydrate diet that has not been administered the substance that is an inhibitor of the enzymatic activity of PTP-1B;

where a difference in the weight gain of the mammal in step (c) as compared with the weight gain of the mammal that has not been administered the substance that is an inhibitor of the enzymatic activity of PTP-1B indicates that the substance regulates obesity in a mammal.

In a particular embodiment, the mammal is a mouse or rat. In another embodiment, the mammal is a human.

The present invention provides substances identified by the above-described method. Such substances are expected to have utility in controlling obesity in humans.

The present invention provides a method of determining whether a substance modulates glucose or triglyceride levels in a mammal that comprises:

(a) transfecting a cell with DNA encoding the human PTP-1B protein;

(b) culturing the cells of step (a) under conditions such that PTP-1B protein is produced;

(c) measuring the enzymatic activity of the PTP-1B protein in the transfected cells in the presence and in the absence of a substance suspected of being an inhibitor of the enzymatic activity of the PTP-1B protein;

where a decrease in the enzymatic activity of the PTP-1B protein in the presence as compared to the absence of the substance indicates that the substance is an inhibitor of the enzymatic activity of the PTP-1B protein;

(d) administering the substance that is an inhibitor of the enzymatic activity of PTP-1B to a mammal;

(e) measuring the blood glucose level or triglyceride levels of the mammal in step (d) and comparing the blood glucose level or triglyceride levels of the mammal in step (d) with the blood glucose level or triglyceride levels of a mammal that has not been administered the substance that is an inhibitor of the enzymatic activity of PTP-1B;

where a difference in the blood glucose level or triglyceride levels of the mammal in step (d) as compared with the blood glucose level or triglyceride levels of the mammal that has not been administered the substance that is an inhibitor of the enzymatic activity of PTP-1B indicates that the substance modulates glucose or triglyceride levels in a mammal.

In a particular embodiment, the mammal is a mouse or rat. In another embodiment, the mammal is a human.

The present invention provides a method of determining whether a substance regulates obesity in a mammal that comprises:

(a) transfecting a cell with DNA encoding the human PTP-1B protein;

(b) culturing the cells of step (a) under conditions such that PTP-1B protein is produced;

(c) measuring the enzymatic activity of the PTP-1B protein in the transfected cells in the presence and in the absence of a substance suspected of being an inhibitor of the enzymatic activity of the PTP-1B protein;

where a decrease in the enzymatic activity of the PTP-1B protein in the presence as compared to the absence of the substance indicates that the substance is an inhibitor of the enzymatic activity of the PTP-1B protein;

(d) administering the substance that is an inhibitor of the enzymatic activity of PTP-1B to a mammal;

(e) measuring the weight gain of the mammal in step (d) when the mammal of step (d) is fed a high fat, high carbohydrate diet and comparing the weight gain of the mammal in step (d) with the weight gain of a mammal fed a high fat, high carbohydrate diet that has not been administered the substance that is an inhibitor of the enzymatic activity of PTP-1B;

where a difference in the weight gain of the mammal in step (d) as compared with the weight gain of the mammal that has not been administered the substance that is an inhibitor of the enzymatic activity of PTP-1B indicates that the substance regulates obesity in a mammal.

In a particular embodiment, the mammal is a mouse or rat. In another embodiment, the mammal is a human.

The present invention includes inhibitors of the enzymatic activity of PTP-1B that have been identified by the above-described methods. Such inhibitors have many uses. For example, such inhibitors can be used in a method of treating obesity comprising administering an inhibitor of the enzymatic activity of PTP-1B to an obese mammal. Such inhibitors can also be used in a method of treating Type II diabetes and associated complications comprising administering an inhibitor of the enzymatic activity of PTP-1B to a person with Type II diabetes.

Such inhibitors are generally combined with pharmaceutically acceptable carriers before use. Examples of such carriers and methods of formulation of pharmaceutically acceptable compositions containing inhibitors and carriers can be found in Remington's Pharmaceutical Sciences. To form a pharmaceutically acceptable composition suitable for effective administration, such compositions will contain an effective amount of the inhibitor.

Therapeutic or prophylactic compositions are administered to an individual in amounts sufficient to treat or prevent obesity or Type II diabetes. The effective amount can vary according to a variety of factors such as the individual's condition, weight, sex and age. Other factors include the mode of administration. The appropriate amount can be determined by a skilled physician.

Compositions can be used alone at appropriate dosages. Alternatively, co-administration or sequential administration of other agents can be desirable.

The compositions can be administered in a wide variety of therapeutic dosage forms in conventional vehicles for administration. For example, the compositions can be administered in such oral dosage forms as tablets, capsules (each including timed release and sustained release formulations), pills, powders, granules, elixirs, tinctures, solutions, suspensions, syrups and emulsions, or by injection. Likewise, they can also be administered in intravenous (both bolus and infusion), intraperitoneal, subcutaneous, topical with or without occlusion, or intramuscular form, all using forms well known to those of ordinary skill in the pharmaceutical arts.

Advantageously, compositions can be administered in a single daily dose, or the total daily dosage can be administered in divided doses of two, three or four times daily. Furthermore, compositions can be administered in intranasal form via topical use of suitable intranasal vehicles, or via transdermal routes, using those forms of transdermial skin patches well known to those of ordinary skill in that art. To be administered in the form of a transdermal delivery system, the dosage administration will, of course, be continuous rather than intermittent throughout the dosage regimen.

The dosage regimen utilizing the compositions is selected in accordance with a variety of factors including type, species, age, weight, sex and medical condition of the patient; the severity of the condition to be treated; the route of administration; the renal, hepatic and cardiovascular function of the patient; and the particular composition thereof employed. A physician or veterinarian of ordinary skill can readily determine and prescribe the effective amount of the composition required to prevent, counter or arrest the progress of the condition. Optimal precision in achieving concentrations of composition within the range that yields efficacy without toxicity requires a regimen based on the kinetics of the composition's availability to target sites. This involves a consideration of the distribution, equilibrium, and elimination of a composition.

The following non-limiting examples are presented to better illustrate the invention.

EXAMPLE 1

Construction of the Targeting Vector

In order to construct the targeting vector, the mouse PTP-1B gene was cloned from a 129/Sv mouse genomic library and characterized. The mouse PTP-1B gene was isolated by screening a Lambda FIX II 129/SvJ mouse genomic library (Stratagene, La Jolla, Calif.) using the human (GenBank accession no. M317324; see also Chernoff et al., 1990, Proc. Natl. Acad. Sci. USA 87:2735–2739) and mouse (GeneBank accession no. M97590; see also Miyasaka et al., 1990, Bioichem. Biophys. Res. Comm. 185:818–825) PTP-1B cDNAs as probes. Three overlapping λ clones were isolated and the genomic organization and exon sequences of the mouse PTP-1B gene were determined. The three λ clones contained the majority of the PTP-1B gene except for the 5' flanking region and the first 190 bp of the cDNA (FIG. 1A). The gene is composed of at least 9 exons spanning greater than 20 kb. A targeting vector (FIG. 1A) was made by deleting genomic sequences that included exon 5 and exon 6 (which contains the tyrosine phosphatase active site cysteine 215) and replacing the deleted sequences with the neomycin-resistance gene. This was accomplished by the cloning of the neo marker gene driven by the PGK promoter (PGK-neo) into the SmaI site of pBluescript KS$^+$ (Statagene, La Jolla, Calif.) (pneoKS). The 5.5 kb Hind III/EcoRI mouse PTP-1B genomic fragment which is just 5' to exon 5 was then inserted into HindIII/EcoRI digested pneoKS. This vector was then digested with XbaI and NotI and ligated with the 1.6 kb XbaI/XhoI mouse PTP-1B genomic fragment which is just 3' of exon 6 and a XhoI/NotI HSV-tk gene driven by the PGK promoter fragment. The resulting targeting vector (pTARGET) was linearized by HindIII digestion.

EXAMPLE 2

Production of Knockout Mice

The targeting vector was electroporated into 129/Sv embryonic stem cells (J1) and G418 resistant colonies were selected as described previously (You-Ten et. al , 1997, J. Exp. Med. 186:683–693). J1 cells are meant to be illustrative only. Other embryonic stem cell lines are suitable as well, e.g., ES-D3 cells (ATCC catalogue no. CRL-1934). Colonies resistant to G418 were analyzed for homologous recombination by BamHI digestion of genomic DNA followed by Southern blotting and hybridization with probe A. Probe A is the 800 bp XhoI/BamHI fragment shown as "3' probe" in FIG. 1A. Approximately 2% of the resistant colonies underwent a homologous recombination event. Two of these G418 resistant ES cell clones were then used for microinjection into Balb/c blactocysts as described previously (You-Ten et. al. , 1997, J. Exp. Med. 186:683–693). Germline transmission was obtained for each line and F1 heterozygotes were mated to produce animals homozygous for the PTP-1B mutation, i.e., null mice. Genotyping was performed by Southern blotting (FIG. 1B). A double band of 3.4 and 2.7 kb is seen in PTP-1B heterozygotic mice and a single band of 2.7 kb is seen in PTP-1B null mice. Immunoblot analysis of liver microsomes revealed that PTP-1B protein was absent in PTP-1B null mice (FIG. 1C). These results demonstrate that the PTP null mice are lacking the PTP-1B enzyme.

EXAMPLE 3

Glucose and Insulin Levels in Knockout Mice Fed a Normal Diet

Figure 2A:
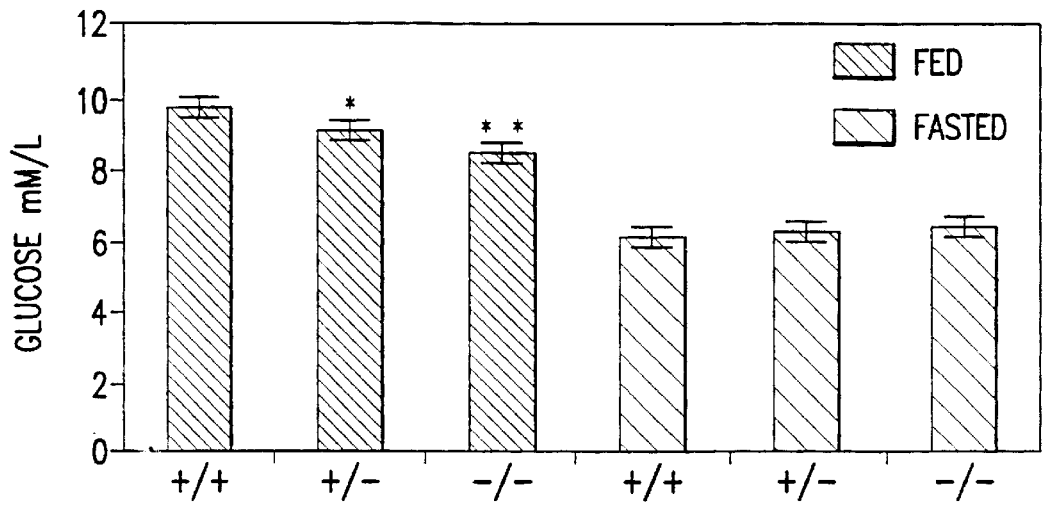
FIG. 2. Glucose and insulin levels in ad libitum-fed and overnight fasted PTP-1B (+/+), PTP-1B (+/−), and PTP-1B (−/−) mice fed on a normal (i.e., non-high fat, non-high carbohydrate) diet. A) Glucose and B) Insulin levels were determined as described in the Examples herein. The number of mice in the fed groups A and B were (n=19–21) and in the fasted group A (n=8–10) and in B (n=6). The values are given as the means ± s.e.m. Statistical analysis was done with a two-tailed unpaired Student's t-test, *, (P=0.06), ** (P≦0.01).
Figure 2B:
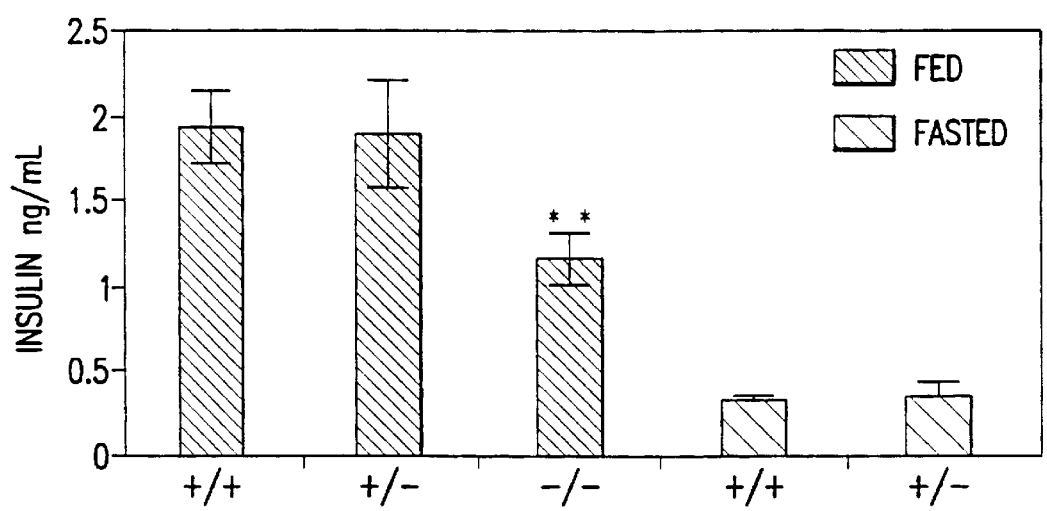

Glucose and insulin levels were measured in fasted and fed mice on a normal, i.e., non-high fat, non-high carbohydrate, diet (FIG. 2). In the fed state the null mice had a significant ($P \leq 0.01$) 13% reduction in blood glucose levels compared to wild-type mice, whereas the heterozygotes had an 8% reduction when compared to wild type (FIG. 2A). Surprisingly, the null mice also had circulating insulin levels that were about half that of wild-type fed animals (FIG. 2B). These results suggest that the fed PTP- 1B-deficient mice are much more sensitive to insulin, resulting in greater glucose lowering in response to much less insulin. In the fasted state, there were no significant differences in glucose or insulin levels among the wild-type, null, and heterozygote mice. However, there was a substantial reduction in triglyceride levels in the fasted state in the PTP-1B null and heterozygote knockout mice as compared to wild-type mice. The triglyceride levels in the fasted null mice (0.86±0.18 mM/L) were about 50% lower than in the wild-type mice (1.84±0.76 mM/L) and were 20% lower in heterozygotes (1.43±0.44). See Table 1.

TABLE 1

| | PTP-1B$^{+/+}$ | | PTP-1B$^{+/-}$ | | PTP-1B$^{-/-}$ | |
|---|---|---|---|---|---|---|
| Diet | Normal | High Fat | Normal | High Fat | Normal | High Fat |
| Glucose (mM/L) | 6.1 ± 0.3 | 8.1 ± 0.6 | 6.2 ± 0.3 | 7.3 ± 0.6 | 6.3 ± 0.3 | 7.0 ± 0.4† |
| Triglycerides (mM/L) | 1.84 ± 0.76 | 2.41 ± 0.19 | 1.43 ± 0.44 | 2.44 ± 0.32 | 0.86 ± 0.18* | 1.46 ± 15* |
| Insulin (ng/ml) | 0.30 ± 0.02 | 0.98 ± 0.32 | ND | 0.97 ± 0.30 | 0.33 ± 0.08 | 0.45 ± 0.14* |

Table 1. Fasting glucose, triglyceride and insulin levels of male PTP-1B (−/−), wild type, and heterozygote littermates fed a normal or a high fat, high carbohydrate diet. The values are given as the means ± s.e.m. Statistical analysis was done with a two-tailed unpaired Student's t-test and compared to wild type.
ND, not determined.
†(P = 0.1),
*(P < 0.05) (n = 6–10)

Triglyceride levels in the fed state were unaffected. These data demonstrate that loss of PTP-1B affects glucose and triglyceride homeostasis in the knockout mice, for the first time strongly implicating PTP-1B in the insulin signaling pathway in an intact mammal.

Figure 3A:
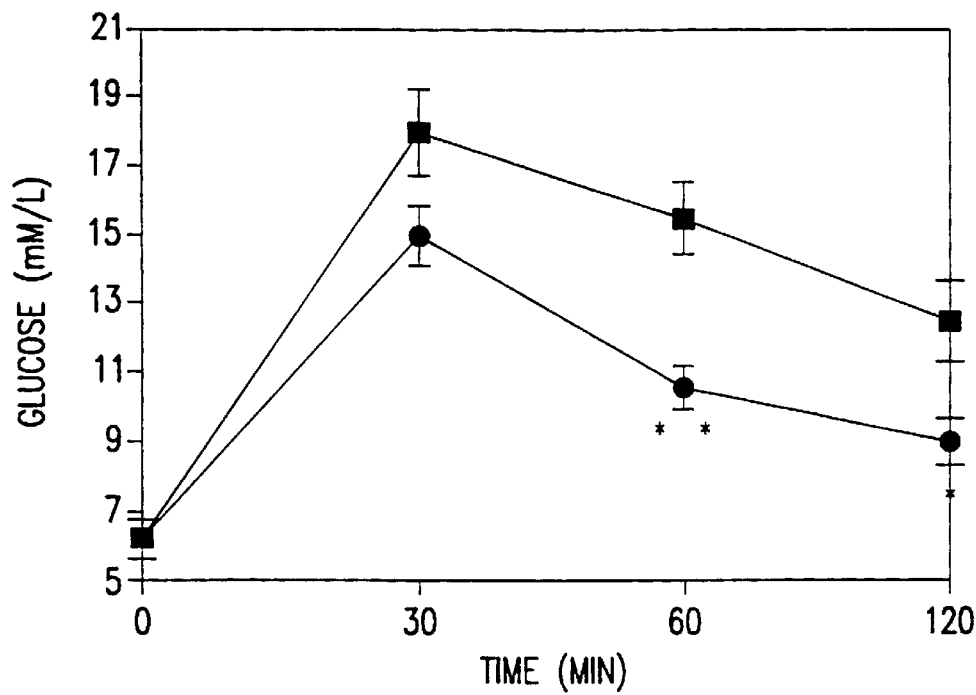
FIG. 3. Glucose and insulin tolerance tests in PTP(+/+) (wild-type) and PTP(−/−) (null) mice fed on a normal (i.e., non-high fat, non-high carbohydrate) diet. A) Glucose tolerance was performed on male mice 10–14-weeks-old (n=11–12); ■=wild-type; ●=null. B) Insulin tolerance on male mice 10–14-weeks-old (n=5–6); ■=wild-type; ●=null. The data are presented as the means ± s.e.m. Statistical analysis was done with a two-tailed unpaired Student's t-test and compared to wild-type, * ($P \leq 0.05$), ** ($P \leq 0.02$).
Figure 3B:
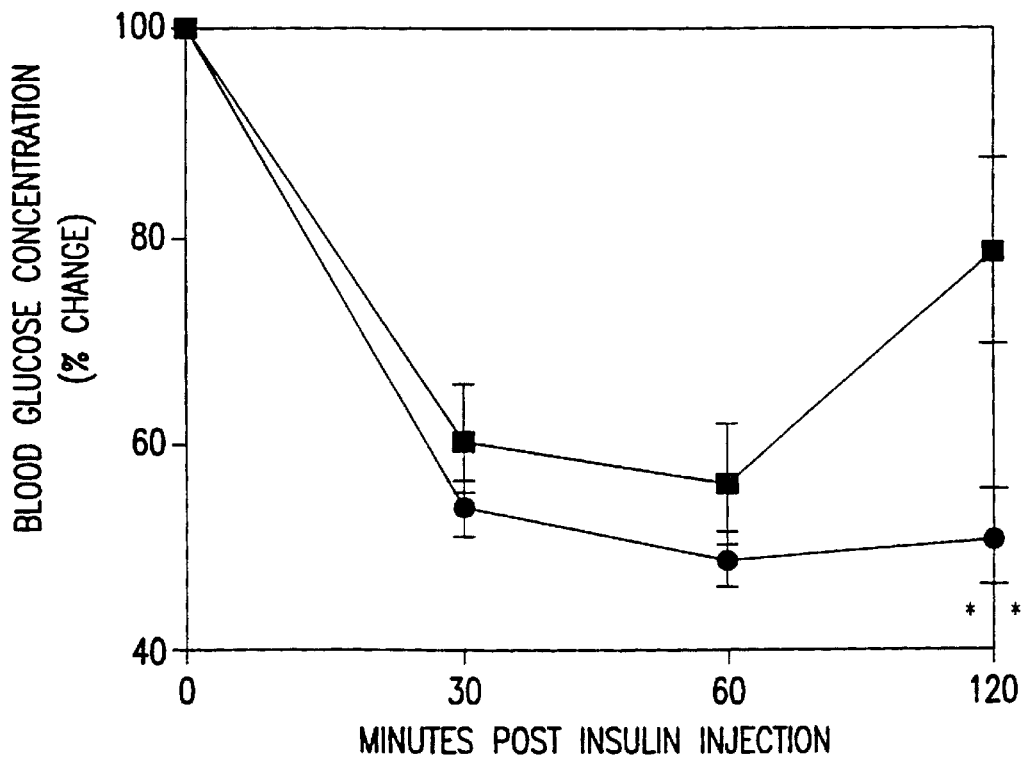

Insulin sensitivity in PTP-1B null and wild-type mice fed a normal diet was further examined by performing oral glucose and intraperitoneal insulin tolerance tests. Administration of a bolus of glucose to PTP-1B null mice resulted in a more rapid clearance of glucose than that observed for wild type mice (FIG. 3A). There was a more pronounced hyperglycemia in the wild type animals at all time points post-gavage when compared to PTP-1B null mice. Increased insulin sensitivity was also observed upon injection of insulin (FIG. 3B). In both null and wild-type mice, hypoglycemia was evident at 30 and 60 minutes post injection. However, whereas wild type glucose levels approached normal levels after 120 minutes, the PTP-1B null mice remained hypoglycemic (P<0.02).

EXAMPLE 4

Figure 4A:
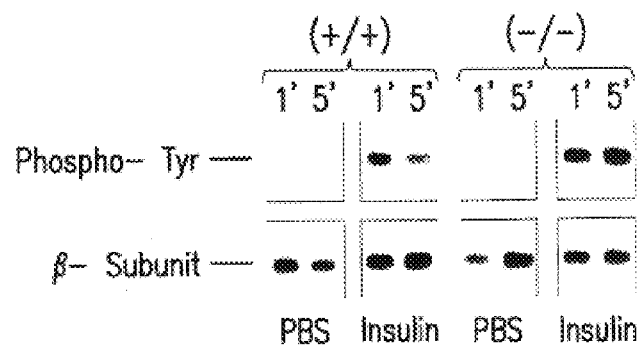
FIG. 4. Disruption of the murine PTP-1B gene results in hyper and prolonged tyrosine phosphorylation of the insulin receptor (IR) in mice fed on a normal (i.e., non-high fat, non-high carbohydrate) diet. A) Representative immunoblot showing the time course of tyrosine phosphorylation on the IR β-subunit after insulin challenge in liver for the times indicated for PTP-1B (+/+) and PTP-1B (−/−) mice. Quantification of the insulin receptor β-subunit phosphotyrosine levels from immunoblots was performed by densitometry. Data is presented by setting the 1 min phosphotyrosine insulin receptor β-subunit level for each animal to 100% and the subsequent 5 min level for the same animal relative to this value. The results are from five PTP-1B (−/−) and PTP-1B (+/+) mice each, from three separate experiments. B) Immunoblot showing the phosphorylation level of the IR β-subunit in muscle from insulin-treated PTP-1B (+/+) and PTP-1B (−/−) mice. The quantified data from the immunoblot (n=3) is given in arbitrary desitometer units with the 2 min time point from the wild type mice set at 100. C) IRS-1 immunoblot from muscle of insulin treated PTP-1B (+/+) and PTP-1B (−/−) mice, 2 minutes post-injection (n=3). In the SDS polyacrylamide (7.5%) gels (15 cm×15 cm) used for the immunoblots, IRS-1 ran as a diffuse 185 kD band. Data are presented as the means ± s.e.m. Statistical analysis was done with a two-tailed unpaired Student's t-test comparing in A) the 5 minute to the 1 mute time point values and in B) the PTP-1B (−/−) mice 2 minute and 6 minute time point values to the respective values of the PTP-1B (+/+) mice, * ($P \leq 0.05$).
Figure 4B:
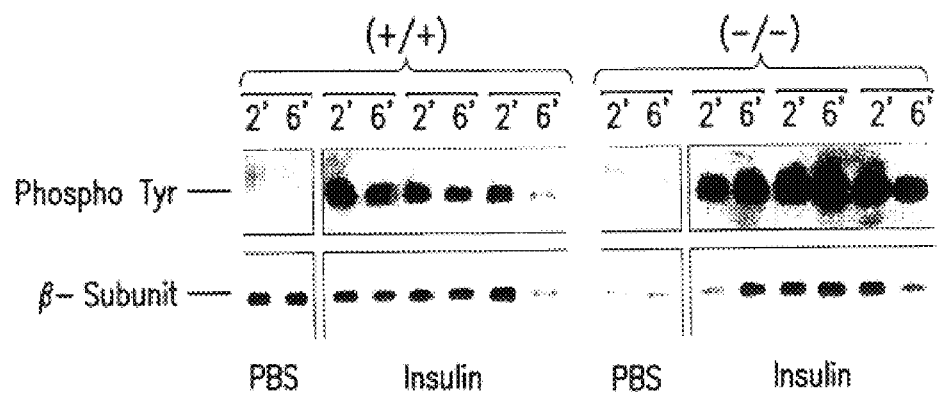

Tyrosine Phosphorylation of the Insulin Receptor and Insulin Receptor Substrate-1 in Knockout Mice To determine whether PTP-1B affects the phosphorylation of the insulin receptor in vivo, i.e., in a living mammal, the phosphotyrosine level of the insulin receptor was measured in both muscle and liver of knockout and wild-type mice after insulin challenge. Insulin was injected as a bolus into the inferior vena cava and tissue samples were taken at various times post-injection in order to determine the time course of insulin receptor dephosphorylation. The insulin receptor β-subunit was then immunoprecipitated from the membrane fraction of tissue homogenates and immunoblotted with an anti-phosphotyrosine antibody to determine the level of phosphorylation of the insulin receptor. The blot was then stripped and reprobed with a C-terminal β-subunit antibody to determine the amount of the β-subunit on the blot in order to normalize the phosphotyrosine signal to the amount of β-subunit. In both null and wild-type mice, in either liver or muscle, the level of insulin receptor phosphorylation in the absence of insulin was very low (FIG. 4A and B). Insulin treatment of wild-type mice resulted in a dramatic increase in the level of insulin receptor tyrosine phosphorylation in the liver (FIG. 4A) which fell to about 50% of the 1 min level by 5 min (FIG. 4A) post-injection (P<0.05). This time course of insulin receptor phosphorylation in the liver has been previously observed in rats with a $t_{1/2}$ of 6 min (Rothenberg et al., 1991, J. Biol. Chem. 266:8302–8311). However, in null mice treated similarly, the kinetics of insulin receptor phosphorylation in the liver were significantly different than those observed for the wild-type mice. The level of insulin receptor phosphorylation was the same for both null and wild-type mice after 1 min post injection, but unlike the wild-type mice, the level of tyrosine phosphorylation in null mice after 5 min post-injection did not decrease and was virtually identical to the 1 min level (P<0.05). The sustained hyperphosphorylation of the insulin receptor in the null mice suggests that the insulin receptor would also remain activated for a much longer period in these mice. However, the most striking effect on insulin receptor hyperphosphorylation was observed in the muscle of the null mice. Analysis of the phosphotyrosine levels of the insulin receptor in muscle samples from insulin treated null mice revealed that there was about a 40% increase in the absolute level of phosphorylation compared to wild-type muscle levels (P<0.05) (FIG. 4B). Unlike the level in liver, the level of insulin receptor phosphorylation in muscle did not decrease over the time course of the experiment in either null or wild-type mice. It is unlikely that the hyperphosphorylation of the insulin receptor observed in the muscle is due to an overexpression of the insulin receptor in null mice, since no detectable difference in the level of insulin receptor expression was observed in either wild-type or null mice as determined by immunoblotting of total tissue lysates. This substantial increase in insulin receptor phosphorylation in the muscle and the sustained phosphorylation of the insulin receptor in the liver of null mice are most likely responsible for the increased insulin sensitivity in these mice. This would also tend to suggest that the ill vivo substrate for PTP-1B, especially in muscle, is the activated insulin receptor.

Figure 4C:
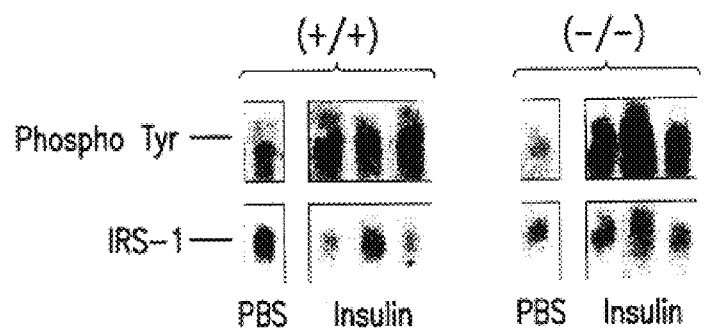
Figures 1, 4A:
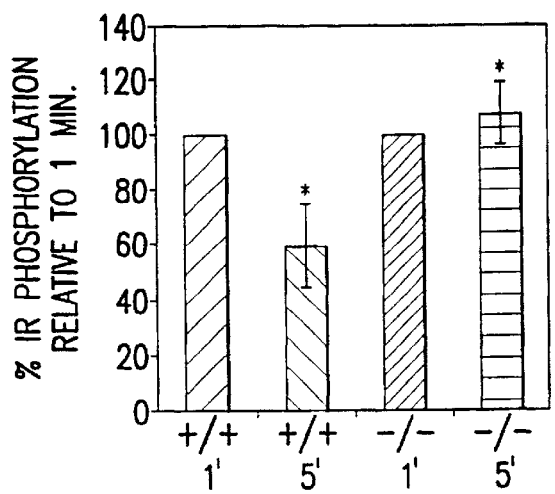
Figures 1, 4B:
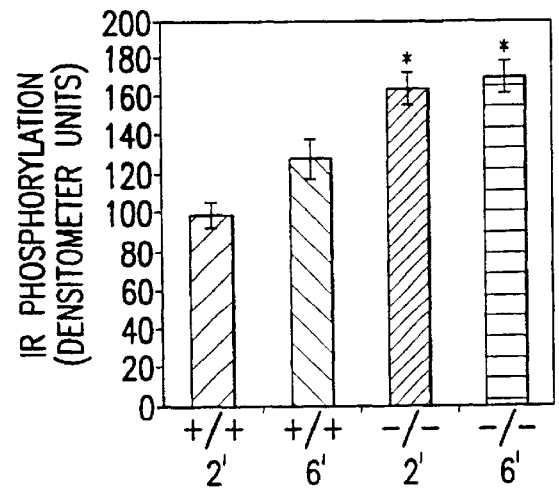
Figures 1, 4C:
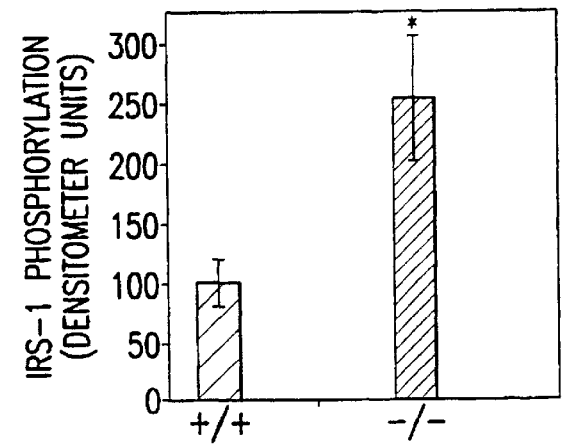

In order to confirm that the hyperphosphorylation of the insulin receptor in the muscle of insulin treated null mice also translates into increased kinase activity, the phosphotyrosine level of the insulin receptor substrate-1 (IRS-1) was examined in the 2 minutes post-injection samples (FIG. 4C). IRS-1 was hyperphosphorylated in muscle of insulin treated null mice compared to wild-type mice (P<0.05). Furthermore, the time course of IRS-1 dephosphorylation in liver has been found to be even more rapid than the insulin receptor, returning to baseline levels after only 2–3 minutes (Rothenberg et al., 1991, J. Biol. Chem. 266:8302–831 1). Nevertheless, hyperphosphorylation of IRS-1, to the same level as the 2 minute time point, was also evident in the 6 minute post-injection null muscle samples.

EXAMPLE 5

Obesity Resistance in PTP-1B Knockout Mice Fed a High Fat, High Carbohydrate Diet Wild-type mice that are fed a high fat, high carbohydrate diet become obese and develop obesity-induced insulin resistance (Uysal et al., 1997, Nature, 389:610–614). Male and female PTP-1B knockout mice (heterozygotes as well as null), 7–8 weeks old, were fed a high fat; high carbohydrate diet (50% calories from fat, 5,286 kcal kg-1, Bio-Serv F3282 mouse diet, Bioserv, Frenchtown, N.J.). As controls, wild-type mice were fed the same diet. After 10 weeks on this diet, both male and female wild type littermates became obese, whereas PTP-1B (−/−) and PTP-1B (+/−) mice were significantly protected from diet-induced obesity (FIG. 5). The starting weights of the animals put on the diet were not significantly different (male, +/+, 27.6±1.4; +/−, 28.5±1.2; −/−, 26.3±1.2 g; and female, +/+, 22.1±0.8; +/−, 22.2±0.8; −/−21.5±0.8 g) while the final weight of the wild type mice when compared to both PTP-1B heterozygotes and null animals (male, +/+, 41.4±1.3; +/−, 37.2±2.0; −/−, 33.5±1.6 g and female, +/+, 33.3±1.7; +/−, 27.3±1.3; −/−27.2±1.4 g) showed a significant difference (P<0.05 wild type versus heterozygotes or null except for male wild type versus heterozygote which was P=0.1). The amount of food consumed by all groups of animals while on the diet did not differ, suggesting that changes in the expression levels of PTP-1B (heterozygotes have about half the level of PTP-1B expression as wild type, FIG. 1C) can affect development of dietary induced obesity.

Figure 6B:
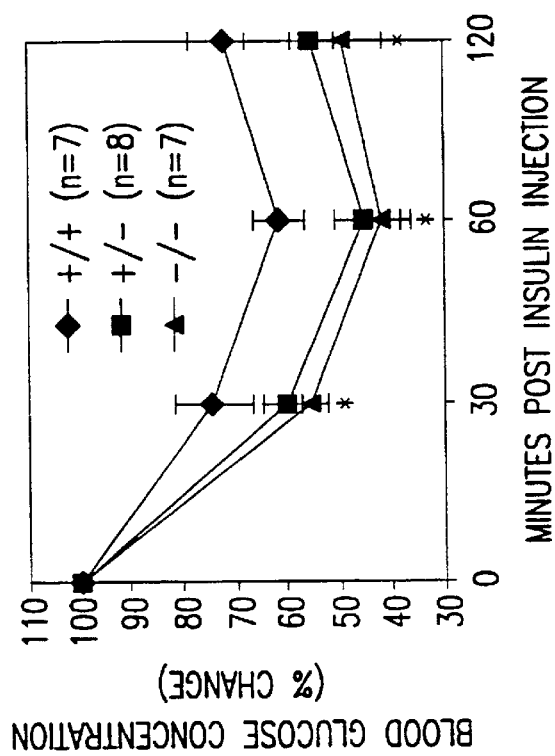
FIG. 6. Glucose and insulin challenge in mice fed a high fat, high carbohydrate diet demonstrating the development of insulin resistance in PTP-1B wild type mice and the relative lack of insulin resistance in PTP-1B knockout mice. A) Glucose and B) insulin tolerance tests of male mice on a high fat, high carbohydrate diet. ♦=wild-type, n=7; ■=heterozygotes, n=7 (A) or 8 (B); ▲=nulls, n=7. C) Insulin-stimulated insulin receptor tyrosine phosphorylation level in muscle in mice fed a high fat, high carbohydrate diet (PTP-1B (−/−) and PTP-1B (+/+), n=2; PTP-1B (+/−), n=3). Quantitation of immunoblots were performed as described in FIG. 4. * ($P \leq 0.05$)
Figure 6A:
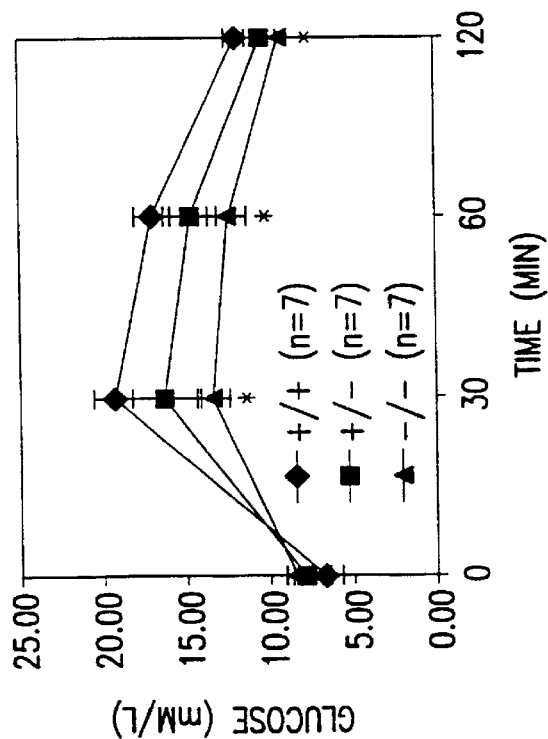
Figure 6C:
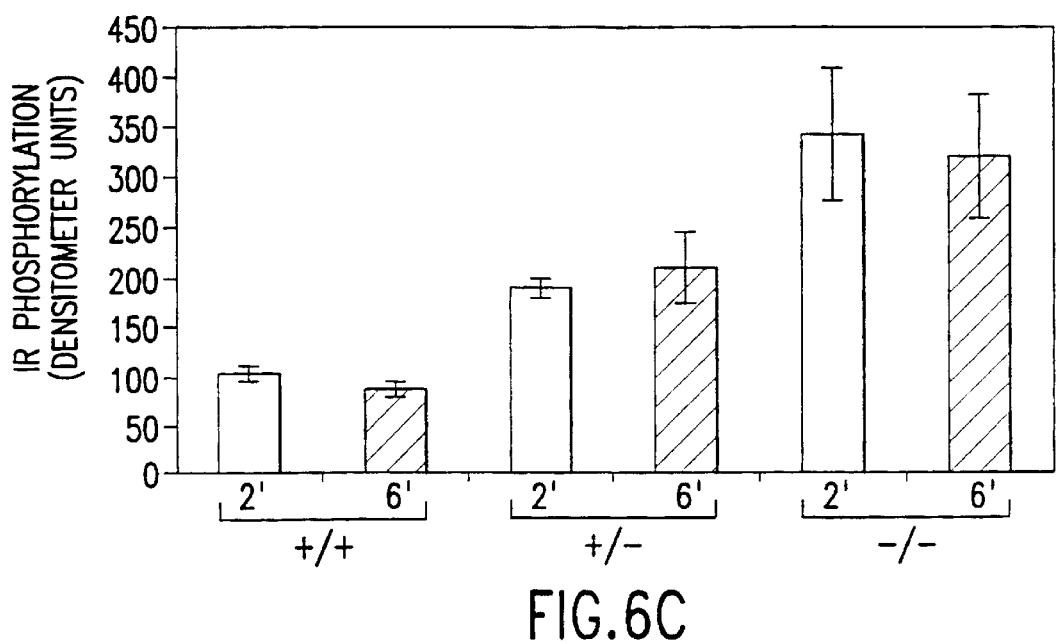

In order to examine the effect the high fat, high carbohydrate diet had on insulin sensitivity in PTP-1B (+/+),PTP-1B (+/−), and PTP-1B (−/−) mice, fasting glucose and insulin levels, as well as glucose and insulin tolerance tests, were performed on all groups of animals (Table 1, above, and FIG. 6; only male values are presented, female values gave essentially the same result). The high fat, high carbohydrate diet produced a 30% increase in fasting glucose levels and a three fold increase in fasting insulin levels in the PTP-1B (+/+) mice (Table 1). In contrast, the PTP-1B (−/−) animals maintained lower glucose and insulin levels while on the high fat diet, levels that are not significantly different from the normal diet values (Table 1). These results indicate that the high fat diet resulted in insulin resistance in the wild type littermates, but not in the PTP-1B (−/−) mice. The fat fed PTP-1B heterozygotes also showed elevated fasting insulin levels but had fasting glucose levels that were lower than wild type (Table 1). Increased insulin sensitivity was also observed in the PTP-1B (−/−) mice compared to their wild type littermates in both glucose and insulin tolerance tests (FIGS. 6A and B), with PTP-1B (+/−) mice appearing to show intermediate sensitivity. The difference in insulin sensitivity between the PTP-1B (−/−) and PTP-1B (+/+) mice as measured by glucose and insulin tolerance became even more evident on the high fat diet (compare FIGS. 3A and B to FIGS. 6A and B). This was also the case when the tyrosine phosphorylation level of the insulin receptor in muscle was measured after insulin challenge in the mice on the high fat, high carbohydrate diet (FIG. 6C). It has been shown that a high fat diet can cause an obesity-related reduction in insulin receptor signaling in muscle and fat tissue (Uysal et al., 1997, Nature, 389:610–614). In FIG. 4B, insulin stimulation of mice fed a normal diet caused about a 40% increase in the phosphotyrosine level of the insulin receptor in muscle of PTP-1B (−/−) compared to PTP-1B (+/+) mice. The high fat diet increased this difference in insulin sensitivity between the wild type and PTP-1B (−/−) mice to the extent that the PTP-1B (−/−) mice have about a 4 fold higher insulin receptor phosphorylation level than wild type, whereas the PTP-1B (+/−) mice show an intermediate level (about 2 fold higher than wild type) (FIG. 6C). The expected phenotype, namely obesity and insulin resistance, was observed for the PTP-1B (+/+) mice fed a high fat diet. In contrast, both PTP-1B (+/−) and PTP-1B (−/−) mice presented an unexpected phenotype in that they were resistant to the development of obesity. Insulin sensitivity was maintained in the PTP-1B (−/−) mice, while the PTP-1B (+/−) mice showed an intermediate sensitivity compared to the PTP-1B wild type and null mice.

The above-described results in mice fed a high fat, high carbohydrate diet demonstrate that PTP-1B knockout mice remain insulin-sensitive on this diet. In fact, they are much more insulin-sensitive than their wild-type littermates. Thus, it would have been expected that PTP-1B knockout mice, when fed on a high fat, high carbohydrate diet, would be at least as susceptible to obesity as wild-type mice, if not more so, since their increased insulin sensitivity would have been expected to induce increased lipogenesis in the knockout mice. However, the experiments described below show that just the opposite occurs.

The weight of the PTP-1B knockout and wild-type mice fed a high fat, high carbohydrate diet, as well as the amount of food the mice consumed, was measured each week. There was essentially no difference in food consumption between wild-type, heterozygote, and null mice. After ten weeks of being on the high fat, high carbohydrate diet, wild type mice had about a 50% weight gain; heterozygote and null mice both had only about a 25–30% weight gain. Thus, the knockout mice have about half the weight gain of wild-type mice when fed a high fat, high carbohydrate diet. See FIG. 5. These results indicate that PTP-1B plays a role in obesity and that inhibitors of the enzymatic activity of PTP-1B will be harmacologically useful in the control of obesity.

EXAMPLE 6

Figure 7A:
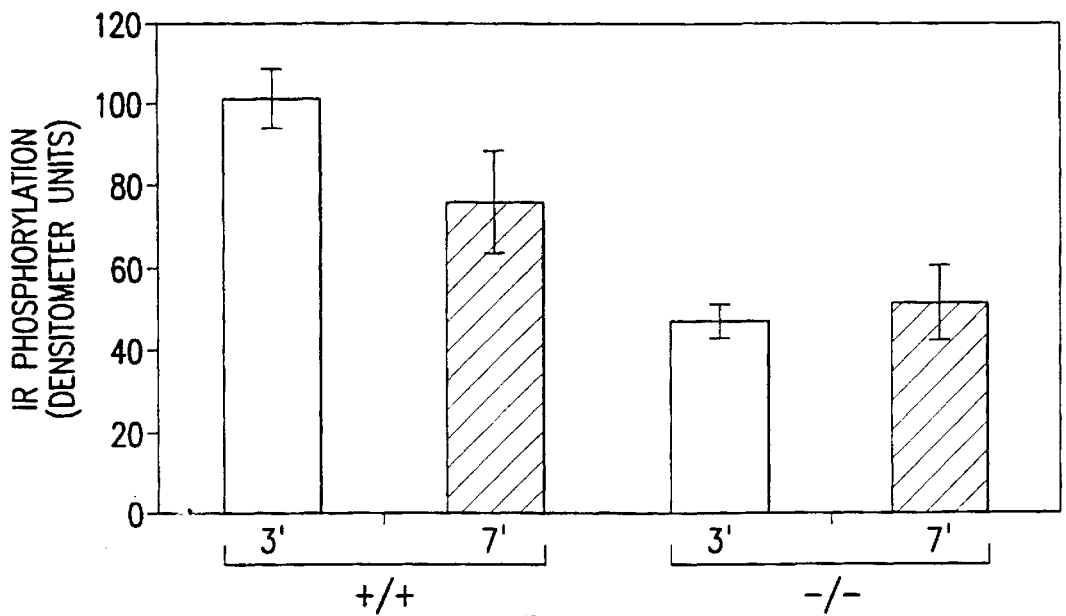
FIG. 7. Tyrosine phosphorylation level of the insulin receptor in fat after insulin challenge in PTP-1B (+/+) and PTP-1B (−/−) mice. Levels of insulin receptor phosphotyrosine in fat from mice on normal diet A) and high fat diet B). Quantitation of immunoblots were performed as described in FIG. 4 setting the 3 min time point of the wild type mice to 100. The data represent the average of two mice from each group ± s.e.m.
Figure 7B:
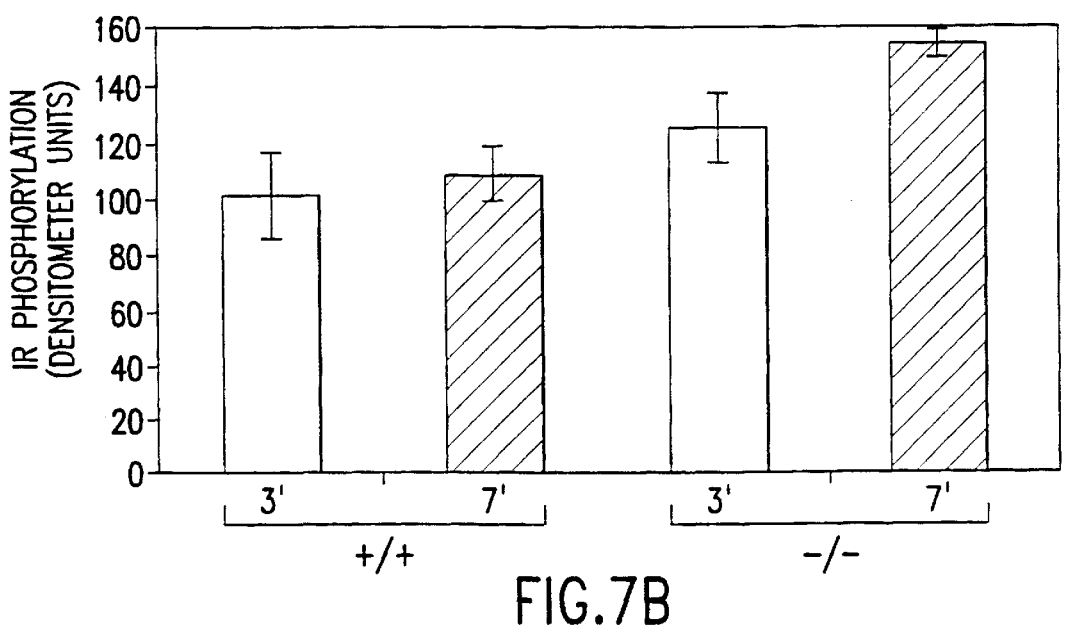

Induction of Uncoupling Protein in White Adipose Tissue of PTP-1B$^{-/-}$ Mice To investigate the reason for the obesity resistance in the PTP-1B (−/−) mice, we measured fasting triglyceride levels in mice on either the high fat or normal diet. The PTP-1B (−/−) mice on either diet had significantly lower triglyceride levels than wild type and heterozygous mice. The PTP-1B (+/−) mice had slightly lower triglyceride levels on the normal diet compared to wild type mice but showed no difference compared to wild type when on the high fat, high carbohydrate diet. This result indicates that the loss of PTP-1B had an effect on fat metabolism. Accordingly, the phosphotyrosine level of the insulin receptor in adipose tissue was examined after insulin challenge in animals fed a normal or high fat diet. Contrary to liver and muscle, which showed hyperphosphorylation of the insulin receptor, there appeared to be a hypophosphorylation of the insulin receptor in fat from PTP-1B (−/−) mice compared to wild type, suggesting that adipose tissue of PTP-1B (−/−) mice may to some extent be insulin resistant (FIG. 7A). Support for this comes from the fact that the high fat fed wild type mice which are insulin resistant now have insulin receptor phosphorylation levels in adipose tissue basically equivalent to that of the PTP-1B (−/−) mice (FIG. 7B). Thus PTP-1B-deficient mice appear to show tissue specific insulin sensitivity. Liver and muscle are more sensitive, whereas fat tissue appears to be resistant, compared to wild type mice.

Figure 8A:
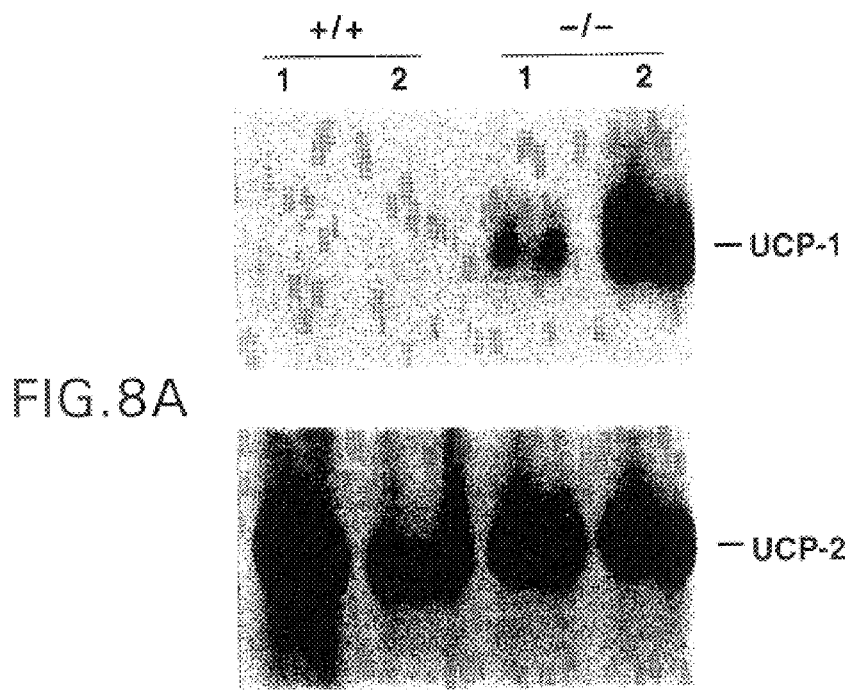
FIG. 8. Induction of uncoupling protein-1 and brown adipocytes in white adipose tissue of PTP-1B (−/−) mice. A) Northern blot analysis of UCP-1 and UCP-2 mRNA expression in abdominal fat of wild type (n=2) and PTP-1B (−/−) mice (n=2). B) Histology of inguinal white adipose tissue (IWAT) from wild type and PTP-1B (−/−) mice showing induction of multilocular adipocytes in PTP-1B (−/−) IWAT. C) Histology of interscapular brown adipose tissue (IBAT) from wild type and PTP-1B (−/−) mice. Note the larger fat droplets in wild type IBAT adipocytes compared to IBAT of PTP-1B (−/−) mice.
Figure 8B:
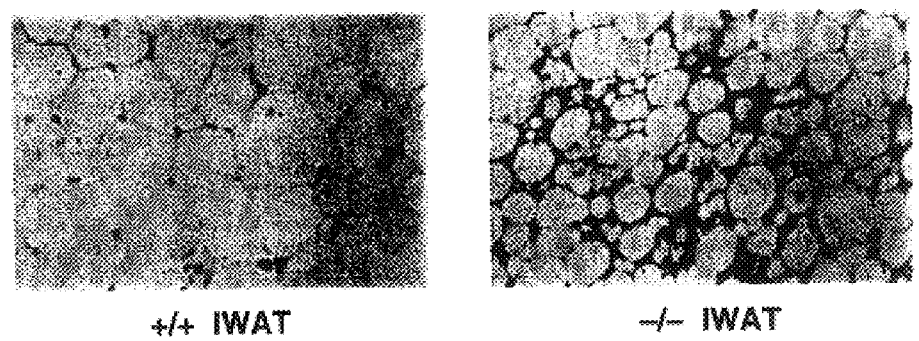
Figure 8C:
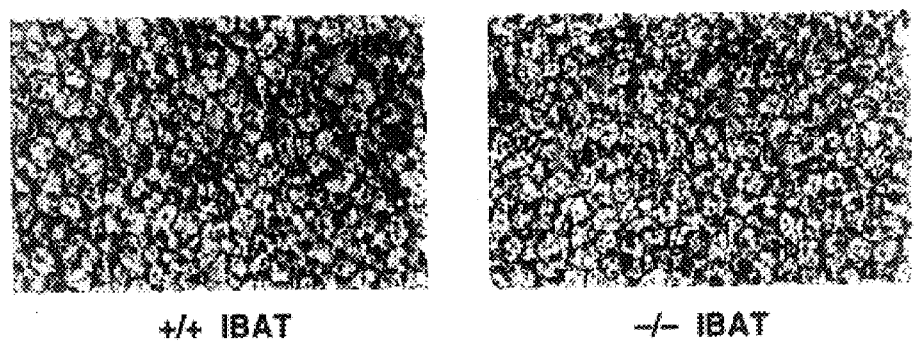

Altered insulin signaling in the fat tissue of the PTP-1B (−/−) mice is likely one of the factors that contributes to the obesity resistance observed in these animals. Insulin action on adipocytes results in decreases in cAMP levels and stimulation of lipogenesis (Manganiello et al., 1996, Curr. Top. Cell. Regul. 34:63–100). In the PTP-1B deficient mice, adipocytes have a reduced insulin response and consequently may be resistant to fat formation. It has been well documented that increasing the activity of protein kinase A (PKA) in adipocytes either by increasing cAMP levels through the action of β adrenergic receptor activity or by altering the PKA regulatory subunits through gene knockout can result in obesity resistance due to the induction of uncoupling protein-1 (UCP-1). UCP-1 is a mitochondrial proton translocator that uncouples the oxidation of fatty acids in BAT. This results in the energy derived from the breakdown of fatty acids being dissipated as heat instead of ATP formation, thus raising the body's resting metabolic rate (Himms-Hagen & Ricquier, 1998, "Brown Adipose Tissue" in *Handbook of Obesity* (eds Bray, G. A, Bouchard, C. & James, W. P. T.) pages 415–441 (Marcel Dekker Inc., New York; Cummings et al., 1996, Nature 382:622–626). If the loss of PTP-1B activity has affected cAMP levels in the adipose tissue of PTP-1B (−/−) mice due to altered insulin receptor activity in adipose tissue, then this may account for the obesity resistance phenotype observed in the PTP-1B (−/−) mice. Northern blot analysis was performed to investigate whether UCP was induced in the white adipose tissue (WAT) of PTP-1B wild type and null mice (normal diet). Induction of UCP-1 mRNA in abdominal WAT of two separate PTP-1B (−/−) mice was apparent, whereas it was undetectable in PTP-1B (+/+) WAT (FIG. 8A). UCP-2 mRNA levels were unchanged between wild type and PTP-1B (−/−) mice (FIG. 8A). UCP-1 mRNA is only expressed in brown adipocytes and its expression in a white adipose depot indicates the induction of brown adipose in this fat depot (Ghorbani et al., 1997, Biochem. Pharmacol. 54:121–131). Histological analysis of inguinal WAT from wild type mice showed the expected typical large unilocular adipocyte (FIG. 8B). In contrast, the inguinal WAT from PTP-1B (−/−) mice contained much smaller unilocular adipocytes and, more importantly, revealed the presence of many multilocular adipocytes not normally found in this fat depot (FIG. 8B). The multilocular adipocyte is characteristic of brown adipose, consistent with the UCP-1 mRNA expression observed in the PTP-1B (−/−) WAT. Immunological staining showed that the multilocular cells in the inguinal WAT from PTP-1B (−/−) mice stained positive for UCP protein. Examination of interscapular BAT (IBAT) revealed that the PTP-1B (+/+) mice contained adipocytes with larger lipid droplets than found in PTP-1B (−/−) mice (FIG. 8C).

EXAMPLE 7

Glucose and Insulin Measurements

Blood was collected from the orbital sinus of anesthetized mice and serum was prepared. Serum glucose levels were determined using a Vitros 250 analyzer and radioimmunoassay (Linco. St.Charles, Mo.) was used to measure insulin levels.

Glucose tolerance was performed after an overnight fast by administration of 1 g/kg of glucose by gavage and blood collected at t=0, 30, 60 and 120 min in anesthetized male mice (10–14-weeks-old). Plasma was prepared and frozen until use and serum glucose levels determined. Insulin tolerance tests were performed after an overnight fast by intraperitoneal injection of 0.75 U/kg of regular human insulin (Eli Lilly, Indianapolis. Ind.). For both glucose tolerance and insulin tolerance tests, blood was collected from the tail of mice and one drop of blood was placed on the One Touch Strip glucose assay system and glucose levels were monitored to the corresponding One Touch Basic (Lifescan Canada Ltd., Burnaby, British Columbia, Canada).

EXAMPLE 8

In vivo Analysis of Insulin Receptor Phosphorylation

After an overnight fast, mice were anesthetized, the abdominal cavity exposed, and 5 units of regular human insulin (Eli Lilly, Indianapolis, Ind.) or saline was injected as a bolus into the inferior vena cava (Araki et al., 1994, Nature 372:186–190). One minute after injection a small piece of liver was excised and immediately frozen in liquid nitrogen. Approximately 2 min after the injection a piece of quadriceps muscle and abdominal fat was removed and quick frozen. This was again repeated at 5, 6, and 7 min post-injection for liver, muscle, and fat, respectively and the mice were then sacrificed before recovery.

EXAMPLE 9

Immunoprecipitation and Immunoblot Analysis

Immunoblot analysis of PTP-1B expression in liver membrane fractions (25 μg/lane) of wild-type, heterozygotic, and null mice was perfomed using an N-terminal specific (amino acids 43–56) PTP-1B rabbit polyclonal antibody (UBI). The blot was developed using enhanced chemiluminescence (NEN). Immunoprecipitation of the insulin receptor β-subunit was performed as follows. The tissue, either liver, fat, or muscle, was homogenized on ice in 50 mM Tris pH 7.5, 150 mM NaCl, 1 mM pyrophosphatc, 100 uM pervanadate (a potent PTPase inhibitor; Huyer et. al., 1997, J. Biol. Chem. 272:843–851) and a protease inhibitor cocktail (Boehringher Mannheim). A membrane fraction was prepared by centrifugation at 100,000×g for 1 h and protein concentration determined. Two hundred μg of liver or muscle membrane protein, or 100 μg of fat membrane protein, was solubilized in immunoprecipitation buffer (RIPA) (150 mM NaCl, 10 mM phosphate buffer pH 7.5 1% NP-40, 1% Na deoxycholate, 0.1% SDS) and immunoprecipitation of the insulin receptor β-subunit was carried out overnight at 4° C. using 1 μg of the anti insulin receptor antibody (C-19) (Santa Cruz Biotechnology, Santa Cruz, Calif.) followed by a 60 min incubation of 50 μl of a 50% slurry of protein G sepharose (Pharmacia Biotech). The sample was washed 3 times in 1 ml of RIPA buffer and samples were loaded on an 8% SDS PAGE. The samples were transferred onto PVDF membrane and immunodetection of phosphotyrosine was performed using the anti-phosphotyrosine 4G10 horse radish peroxidase coupled antibody (Upstate Biotech) according to the manufacturer's protocol. The same blot was stripped in 62.5 mM Tris pH 6.7, 2% w/v SDS, 100 mM β-mercaptoethanol for 30 min at 55° C., washed, and reprobed with the anti insulin β-subunit Rb (C-19, Santa Cruz Biotechnology, Santa Cruz, Calif.). The phosphotyrosine signal and β-subunit levels were then quantiated by densitometry (Molecular Dynamics) and phosphotyrosine levels normalized to the amount of β-subunit present in each sample. Immunoprecipitation of IRS-1 was performed with two IRS-1 rabbit polyclonal antibodies (C-20, C-terminus specific and A-19, N-terminus specific, Santa Cruz Biotechnology, Santa Cruz, Calif.) using the cytosolic fraction from muscle of insulin treated mice, as described above.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference in their entireties.

8. The mouse of claim 7 wherein the PTP-1B gene is disrupted by the insertion of a plasmid comprising a selectable marker gene.

9. The mouse of claim 7 wherein the PTP-1B gene is disrupted by the insertion of pTARGET.

10. The mouse of claim 7 wherein the mouse has about half the weight gain of wild-type mice when fed a high fat, high carbohydrate diet.

11. A transgenic mouse whose genome is homozygous for a disrupted PTP-1B gene, such that said mouse has no detectable PTP-1B, and wherein said mouse exhibits a phenotype selected from the group consisting of mice hav-

What is claimed:

1. A transgenic mouse whose genome is homozygous for a disrupted PTP-1B gene, such that said mouse has no detectable PTP-1B, and wherein said mouse exhibits increased insulin sensitivity as compared to wild-type mice.

2. The mouse of claim 1 wherein the PTP-1B gene is disrupted by the insertion of a plasmid comprising a selectable marker gene.

3. The mouse of claim 2 wherein the PTP-1B gene is disrupted by the insertion of pTARGET.

4. The mouse of claim 1 wherein the mouse has about half the level of circulating insulin in the fed state as compared to wild-tape mice.

5. The mouse of claim 1 wherein the mouse has about 13% of the level of blood glucose in the fed state as compared to wild-type mice.

6. A cell line established from the transgenic mouse of claim 1, wherein the cells have no detectable PTP-1B.

7. A transgenic mouse whose genome is homozygous for a disrupted PTP-1B gene, such that said mouse has no detectable PTP-1B, and wherein said mouse exhibits resistance to diet induced obesity as compared to wild-type mice.

ing about half the level of circulating insulin in the fed state as compared to wild-type mice, having about 13% of the level of blood glucose in the fed state as compared to wild-type mice and having about half the weight gain when fed a high fat, high carbohydrate diet as compared to wild-type mice.

12. A method of producing a mouse whose genome is homozygous for a disrupted PTP-1B gene, such that said mouse has no detectable PTP-1B, the method comprising:

(a) providing a gene encoding an altered form of PTP-1B designed to target the PTP-1B gene of mouse embryonic stem (ES) cells, wherein the form comprises a disruption such that no detectable PTP-1B is produced;

(b) introducing the gene encoding an altered form of PTP-1B into mouse ES cells;

(c) selecting ES cells in which the altered gene encoding an altered form of PTP-1B has disrupted the wild-type PTP-1B gene;

(d) injecting the ES cells from step (c) into mouse blastocysts;
(e) implanting the blastocysts from step (d) into a pseudopregnant mouse;
(f) allowing the blastocysts to develop into embryos and allowing the embryos to develop to term in order to produce a mouse homozygous for a disrupted PTP-1B gene.

13. A transgenic mouse whose genome is heterozygous for a disrupted PTP-1B gene, wherein said disrupted gene in a homozygous state produces a mouse that has no detectable PTP-1B, and wherein said mouse exhibits increased insulin sensitivity as compared to wild-type mice.

* * * * *

UNITED STATES PATENT AND TRADEMARK OFFICE
CERTIFICATE OF CORRECTION

PATENT NO. : 6,605,753 B1  Page 1 of 1
DATED : August 12, 2003
INVENTOR(S) : Brian Kennedy et al.

It is certified that error appears in the above-identified patent and that said Letters Patent is hereby corrected as shown below:

<u>Title page,</u>
Item [73], Assignee, delete "Merck & Co., Inc., Rahway, NJ (US);" and insert
-- Merck Frosst Canada & Co., Kirkland, Quebec, (CA); --

Signed and Sealed this

Tenth Day of February, 2004

JON W. DUDAS
*Acting Director of the United States Patent and Trademark Office*

```
                           SEQUENCE LISTING

<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<221> NAME/KEY: SITE
<222> LOCATION: 1
<223> OTHER INFORMATION: Xaa = Ile or Val
<220> FEATURE:
<221> NAME/KEY: SITE
<222> LOCATION: 4
<223> OTHER INFORMATION: Xaa = Any Amino Acid
<220> FEATURE:
<221> NAME/KEY: SITE
<222> LOCATION: 7
<223> OTHER INFORMATION: Xaa - Any Amino Acid
<220> FEATURE:
<221> NAME/KEY: SITE
<222> LOCATION: 8
<223> OTHER INFORMATION: Xaa = Any Amino Acid
<220> FEATURE:
<221> NAME/KEY: SITE
<222> LOCATION: 10
<223> OTHER INFORMATION: Xaa = Ser or Thr
<220> FEATURE:
<223> OTHER INFORMATION: Protein tyrosine phosphatase catalytic domain
      consensus sequence

<400> SEQUENCE: 1

Xaa His Cys Xaa Ala Gly Xaa Xaa Arg Xaa Gly
 1               5                  10
```